(12) United States Patent
Hirabayashi et al.

(10) Patent No.: US 8,597,576 B2
(45) Date of Patent: Dec. 3, 2013

(54) ANALYZER FOR GLYCAN OR COMPLEX CARBOHYDRATE

(75) Inventors: Jun Hirabayashi, Ibaraki (JP); Atsushi Kuno, Ibaraki (JP); Noboru Uchiyama, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 13/213,596

(22) Filed: Aug. 19, 2011

(65) Prior Publication Data
US 2012/0053089 A1 Mar. 1, 2012

Related U.S. Application Data

(63) Continuation-in-part of application No. 11/917,921, filed as application No. PCT/JP2006/311950 on Jun. 14, 2006, now abandoned.

(30) Foreign Application Priority Data

Jun. 23, 2005 (JP) .............................. 2005-184171

(51) Int. Cl.
*G01N 21/00* (2006.01)
(52) U.S. Cl.
USPC ........... 422/82.05; 422/52; 422/402; 435/7.1; 435/6.16
(58) Field of Classification Search
USPC ............... 435/7.1, 6.16, 325; 422/400, 82.05
See application file for complete search history.

(56) References Cited

U.S. PATENT DOCUMENTS

| 5,843,651 | A | * | 12/1998 | Stimpson et al. | ............ 435/6.11 |
| 6,214,560 | B1 | * | 4/2001 | Yguerabide et al. | ............ 506/3 |
| 7,056,678 | B1 | | 6/2006 | Markman | |
| 7,132,251 | B1 | | 11/2006 | Markman | |
| 2003/0232382 | A1 | * | 12/2003 | Brennan et al. | ............ 435/6 |

(Continued)

FOREIGN PATENT DOCUMENTS

| EP | 1211514 | 6/2002 |
| JP | 8-201382 | 8/1996 |

(Continued)

OTHER PUBLICATIONS

Roche Applied Science Biochemica Instrument System Version, vol. 1, 2002, pp. 1-12, accompanied by an English language translation of p. 9.

(Continued)

*Primary Examiner* — Sally Merkling
(74) *Attorney, Agent, or Firm* — Greenblum & Bernstein, P.L.C.

(57) ABSTRACT

An analyzer of the present invention for analyzing a glycan or a complex glycan includes a substrate, a fluorescent labeling excitation means and a fluorescent intensity measurement means. The substrate comprises a rectangle photoconductive base plate coated by a compound containing an active group to fix protein by an amino group thereof, one and more open-topped reaction vessel formed on a surface of the base plate, and plural spots of glycan binding proteins arranged in a matrix and immobilized on the surface of the base plate in the reaction vessel. The fluorescent labeling excitation means which excites fluorescent label by generating evanescent-waves on the surface of the substrate comprises a pair of optical fibers arranged toward the both side end faces of the right and left of the substrate to introduce a light thereinto.

21 Claims, 13 Drawing Sheets

(56) References Cited

U.S. PATENT DOCUMENTS

| | | |
|---|---|---|
| 2006/0194269 A1 | 8/2006 | Markman |
| 2007/0092915 A1 | 4/2007 | Markman et al. |
| 2007/0202535 A1 | 8/2007 | Hirabayashi et al. |
| 2008/0254481 A1* | 10/2008 | Love et al. ............... 435/7.1 |

FOREIGN PATENT DOCUMENTS

| | | |
|---|---|---|
| JP | 8-201383 | 8/1996 |
| JP | 2001-520104 | 10/2001 |
| JP | 2002-544485 | 12/2002 |
| WO | 96/35940 | 11/1996 |
| WO | 99/19892 | 4/1999 |
| WO | 01/16600 | 3/2001 |
| WO | 2005/064333 | 7/2005 |

OTHER PUBLICATIONS

X. Zeng et al. "Analysis of specific interactions of synthetic glycopolypeptides carrying N-acetyllactosamine and related compounds with lectins", Carbohydrate Research, vol. 312, 1998, pp. 209-217.

I. Okazaki et al. "BIACORE Applications for Glycoconjugate Research", Trends in Glycoscience and Glycotechnology, vol. 10, No. 54, 1998, pp. 321-329.

L. J. Holt et al. "By-passing selection: direct screening for antibody-antigen interactions using protein arrays", Nucleic Acids Research, vol. 28, No. 15, 2000, e72, pp. i-v.

D. Guschin et al. "Manual Manufacturing of Oligonucleotide, DNA, and Protein Microchips", Analytical Biochemistry, vol. 250, 1997, pp. 203-211.

A. Lueking et al. "Protein Microarrays for Gene Expression and Antibody Screening", Analytical Biochemistry, vol. 270, 1999, pp. 103-111.

P. Mitchell, "A perspective on protein microarrays", Nature Biotechnology, vol. 20, 2002, pp. 225-229.

H. Zhu et al. "Global Analysis of Protein Activities Using Proteome Chips", Science, vol. 293, 2001, pp. 2101-2105.

H. Zhu et al. "Analysis of yeast protein kinases using protein chips", Nature Genetics, vol. 26, 2000, pp. 283-289.

Extended European search report, including the Supplementary European search report and the European search opinion, mailed Sep. 2, 2010, that issued with respect to European Patent Application No. 06766719.6.

S. Angeloni et al., "Glycoprofiling with micro-arrays of glycoconjugates and lectins," Glycobiology, vol. 15, No. 1, Jan. 2005, pp. 31-41, XPO02593406 ISSN: 0959-6658, Jan. 2005.

Blixt et al. (PNAS, Vo;. 101 No. 49 Dec. 7, 2004).

Hirabayashi et al. (Nature Methods vol. 2 No. 11, Nov. 2005).

Array Pro Analyzer (v 4.5) product description, Jan. 1, 2002.

Blixt et al. (PNAS Dec. 7, 2004, vol. 101 No. 49).

Hirabayashi (Glycoconjugate Journal 21, 35-40, 2004).

Product description for IMAGENE image analysis software, Feb. 20, 2008.

Osborne et al. (Progress in Organic Coatings 41 (2001) 226-232).

N. Uchiyama et al., "Development of lectin-microarrays to profile glycoprotein glycosylation under equilibrium conditions with an evanescent field fluorescence detection principle," Glycobiology, Oxford University Press, US, vol. 14, No. 11, Nov. 1, 2004, p. 1189, XP009088873 ISSN: 0959-6658, Nov. 1, 2004.

S. Park et al., "Fabrication of carbohydrate chips for studying protein-carbohydrate interactions," Angewandte Chemie (International Ed. in English) Sep. 2, 2002, LNKD-PUBMED:12207382, vol. 41, No. 17, Sep. 2, 2002, pp. 3180-3182, ISSN: 1433-7851, Sep. 2, 2002.

A. Kuno et al., "Evanescent-field fluorescence-assisted lectin microarray: a new strategy for glycan profiling" Nature Methods, Nature Publishing Group, GB LNKD-DOI: 10.1038/NMETH803, vol. 2, No. 11, Nov. 1, 2005, pp. 851-858, XP009088872 ISSN: 1548-7091, Nov. 1, 2005; also submitted as html version obtained from: http://www.nature.com/nmeth/journal/v2/n11/full/nmeth803.html.

* cited by examiner

ANALYZER FOR GLYCAN OR COMPLEX CARBOHYDRATE

RELATED APPLICATIONS

The present application is a continuation in part of U.S. patent application Ser. No. 11/917,921, now abandoned, which was a National Phase application of PCT/JP2006/311950, filed Jun. 14, 2006, which claims priority to Japanese Application No. JP2005-184171, filed Jun. 23, 2005, which are all hereby incorporated by reference herein in their entireties.

TECHNICAL FIELD

The present invention concerns an analyzer for a glycan or a complex carbohydrate, or a sample containing the same by utilizing an evanescent light.

BACKGROUND ART

In order that a protein as a main part responsible to the life function of a living body exerts its function orderly in the cell population, modification after translation including modification of a glycan has an extremely important role. In recent years, it has been found continuously that almost of proteins in living bodies undergo modification by glycans and that glycans added to proteins play an important role in various fields of life phenomena such as infection of virus, parasitism and infection of protozoa, binding of toxin, binding of hormone, conception, emergence and differentiation, stability of protein, cancer cell metastatsis, and apoptosis.

For analyzing a glycan function, the structural analysis for the glycan is first indispensable. It is expected that more importance will be attached to the glycan structure analysis method in the future. However, since the structural analysis of the glycan requires enormous time, energy, and experience it has been expected develop a system capable of extracting the features of various glycan structures more conveniently, quickly, at a higher sensitivity and higher accuracy and capable of distinguishing them from each other, instead of aiming at a complete determination of structure based on the existent method.

A micro-array is a collective name of instruments in which immobilized specimens such as various types of DNA-proteins are immobilized spot-wise at a high density on a solid phase carrier (glass membrane silicon chip) and this can detect the presence or absence of molecules binding specifically to various types of immobilized specimen spots (hereinafter referred to as a probe). For the probe molecules, those labeled with fluorescence are generally used and, by reacting a probe solution with an array surface and then observing by a fluorescent detection scanner, quantitative analysis can be conducted for the probe molecules binding to each of specimen spots. Since a DNA micro-array was developed by Affymetrix Co in USA, micro-arrays have been used in an extremely wide variety of fields of study to provide various novel findings to human beings.

For the study of structural and functional information on glycans which are referred to as the third life chain, in a case where interaction of glycans and proteins showing interaction with the glycan (glycan binding protein, for example, lectin) can be analyzed quickly at a high sensitivity in a large scale by utilizing the micro-arrays, it is considered that this may provide an extremely useful tool that can be utilized in a wide range from the basic study to medical diagnosis or industrial application.

It has been known that binding between the glycan and the protein that exhibits the interaction with the glycan is generally a weak interaction compared with a general dissociation constant of an antigen-antibody reaction ($Kd=10^{-8}$ M or less), and the dissociation constant (Kd) thereof is often $10^{-6}$ M or more. Further, it has been known that binding between the glycan and the protein that exhibits the interaction with the glycan comprises relatively fast dissociation and association reaction and, as a result, the equilibrium tends to direct to the dissociation side by a cleaning operation or the like compared with general inter-protein interaction or interaction between complementary nucleotide fragments. For example, also in a case of purifying a lectin by a glycoside protein immobilization column or the like, when the lectin binding is weak, a phenomenon has often been observed that lectin runs off to the outside of a column during the cleaning operation.

In the general existent micro-array technique using a slide glass, after the process of bringing a probe solution into contact with an immobilizing specimen to cause binding reaction, operations of cleaning and removing the probe solution and completely removing the water content deposited on the slide glass are conducted by using a jet gas or a centrifugator, and then imaging is conducted by using a micro-array scanner. This is because fluorescence on the slide glass can not be observed by a general micro-array reader in a state where the water content is deposited. Even when the probe solution is removed in a stage before the scanning, it is considered that the dissociating reaction of the probe molecules does not proceed easily since the dissociation rate constant is sufficiently small in the interaction showing strong bond such as complementary nucleotide fragment or antigen-antibody reaction. However, upon observation of the interaction of high, dissociation rate constant, that is, weak interaction shown generally between the glycan and the protein that exhibits interaction with the glycan, the dissociation reaction proceeds between the glycan and the protein that exhibits interaction with the glycan at the instance of conducting the removing and cleaning operation for the probe solution and it is difficult to obtain an accurate interaction information under the equilibrium state. Accordingly, in the micro-array, the cleaning operation of the probe solution results in a significant problem in a case of precisely analyzing the interaction information in the equilibrium state between the glycan and the protein that exhibits interaction with the glycan.

DNA micro-arrays have been utilized in an extremely wide range at present. Also for protein micro-arrays, future utilization is expected in the field of basic study such as clarification of the function of a protein as the product of DNA transcription in the living body, as well as in the application field such as diagnosis or judgment on the basis of quantitative or qualitative change of the protein, and vigorous researches have been conducted all over the world in view of the study. However, development and popularization for the protein micro-array is greatly delayed compared with that for the DNA micro-array. As one of the causes, it has been pointed out by various workers that a step of immobilizing protein specimens having various different natures at a predetermined ratio in a state of keeping the activity as it is extremely difficult technically.

For the methods of immobilizing proteins on arrays, a method developed in the earliest stage includes a method of physically adsorbing a protein on a membrane typically represented by a PVDF (Non-Patent Document 1). It has been reported that some proteins such as transcription factors can maintain the activity to some extent but it lacks in generality. Further, in a case of immobilization on the membrane, increase in the density of the array has been limited. For obtaining higher density, while a study has been progressed in the direction of immobilizing the protein to the surface of a solid such as metal or glass, the protein generally has a nature tending to be denatured by the contact with the surface of the solid such as metal or glass. Accordingly, an immobilizing method using a certain linker for crosslinking the surface of the solid and the protein has been studied and developed vigorously.

An example of the method of mitigating the problem of denaturation of the protein includes a method of joining a pad of a polyacrylamide of 10 to 100 μm thickness on a slide glass and spotting the protein thereto (Non-Patent Documents 2 and 3). In this case, since the protein is immobilized in a three-dimensional space, it is said that improvement by 100 times or more may be expected in view of the quantity compared with a method of immobilizing on a two-dimensional surface. Further, there is also a method of immobilizing the protein by way of an amino group in a porous polyacrylamide gel (Non-Patent Document 4). However, the methods described above have not yet been popularized generally since it is necessary to prepare a expensive and special slide glass. Further, the immobilized protein layer has a thickness and this is sometimes not preferred depending on the detection method.

Further, Patent Document 4 discloses a photoconductive substrate having a closed type reaction vessel with spots of glycan binding protein, and teaches technology to introduce light from one side edge of the substrate so as to detect fluorescence excited by evanescent waves generating on the surface of substrate.

However, reagent is supplied into the vessel only by using capillary action, since the reaction vessel is formed in a closed gap between two layered glass plates. That is, it wastes long time, reagent can not be supplied to the vessel momentarily, especially under monitoring condition.

Since the light is introduced from one side edge of the substrate, intensity of scattered light of evanescent wave at the one side of substrate is higher than intensity at another side.

Therefore evanescent waves generated on the surface of the substrate can not be uniform, and measurement accuracy is reduced.

Methods of immobilizing proteins to the solid phase that have been being studied most vigorously at present include a method of expressing a protein in a form attached with some or other tag and immobilizing the protein by way of its tag portion to a solid phase carrier. It has been said for the method that it can provide an effect of improving the effective ligand concentration of the protein or alignment for the direction of the protein in principle. An example of such method includes a method of immobilization by way of oligohistidine tag to a substrate modified at the surface with a nickel complex (Non-Patent Document 5) or a method of immobilization by way of avidin-biotin (Patent Document 1).

It is considered that such methods are effective in immobilization while keeping the activity of the protein as it is, or making the rate of immobilization uniform. However, since it is considered to require much cost and enormous labor for adding tags at the gene level to all proteins to be immobilized on the micro-array and conducting expression by *Escherichia coli* bacteria or non-cell systems and purification, it is difficult for usual workers to easily utilize the method optionally and in the form conforming with individual requirements.

On the contrary, a method of utilizing functional groups of proteins for immobilization with solid phase carrier has a feature that proteins as extracted from natural products or commercial protein specimens can be immobilized as they are and utilized for the micro-array. A method of immobilization by way of amino groups in proteins to a solid phase carrier includes a method of immobilizing a protein by way of active ester groups bonded on the surface of the solid phase, or a method of immobilizing a protein by way of epoxy groups arranged on the surface of the solid phase (Non-Patent Document 6). While the method of immobilization by way of the amino groups of the protein is a simple method, since commercial proteins, bio-body extract ingredients, or recombinant proteins with no particular tags can also be immobilized simply and conveniently, individual users can optionally select proteins in accordance with the object of their own and can use them with optimization to micro-arrays conforming with the purpose rapidly and at a low cost. Drawbacks of the immobilizing method by way of the amino groups of the protein include, for example, that the number of lysine residues in the proteins is different depending on individual proteins or that inactivation of the protein may possibly occur depending on the position of the lysine residues used for immobilization.

Patent Document 1: JP-A No. 2001-520104
Patent Document 2: JP-A No. 8-201382
Patent Document 3: JP-W No. 2002-544485
Non-Patent Document 1: L. J. Holt, K. Bussow, G. Walter, I. M. Tomlinson, Nucleic Acids Res. 15, E72, 2000
Non-Patent Document 2: D. Guschin, G. Yershov, A. Zaslavsky, A. Germmell, V. Shick, D. Proudnikov, P. Arenkov, A. Mirzabekov, Anal. Biochem., 250, 203-211, 1997
Non-Patent Document 3: A. Lueking, M. Horn, H. Eickhoff, K. Bussow, H. Lehrach, G. Walter, Anal. Biochem., 270, 103-111, 1999.
Non-Patent Document 4: P. Mitchell, Nat. Biotechnol., 20, 225-229, 2002
Non-Patent Document 5: H. Zhu, M. Bilgin, R. Bangham, D. Hall, A. Casamayor, P. Bertone, N. Lan, R. Jansen, S. Bidlingmaier, T. Houfek, T. Mitchell, P. Miller, R. A. Dean, M. Gerstein, M. Snyder, Science, 293, 2101-2105, 2001
Non-Patent Document 6: H. Zhu, J. F. Klemic, S. Chang, P. Vertone, A. Casamayor, K. G. Klemic, D. Smith, M. Gerstein, M. A. Reed, M. Shyder, Nat. Genetics. 26, 283-289, 2000

DISCLOSURE OF THE INVENTION

Subject to be Solved by the Invention

An object of the present invention is to provide more convenient, more quick, more sensitive and more accurate analyzer for analyzing a glycan or a complex glycan, or a specimen containing the same.

Means for Solving the Subject

For solving the subject, the present invention is regarding an analyzer for fluorescence-labeling a glycan to be detected or a complex carbohydrate to be detected with or without purification,
measuring the binding state of the glycan or the complex carbohydrate and a protein thereby, and
analyzing the glycan to be detected or the complex carbohydrate to be detected, or a specimen containing the same,
including
   a substrate comprising
   a rectangle photoconductive base plate coated by a compound containing an active group to fix protein by an amino group thereof,
   one and more open-topped reaction vessel formed on a surface of the base plate, and plural spots of glycan binding proteins arranged in a matrix and immobilized on the surface of the base plate in the reaction vessel;

a fluorescent labeling excitation means which excites fluorescent label by generating evanescent-waves on the surface of the substrate comprises a pair of optical fibers arranged toward the both side end faces of the right and left of the substrate to introduce a light thereinto; and a fluorescent intensity measurement means for measuring the intensity of fluorescence generated by the fluorescent labeling excitation means on every spots of arranging the glycan binding protein.

Preferably, the surface of the photoconductive base plate is covered by a light blocking rubber opening holes at the positions corresponding to areas of the reaction vessels so that the reaction vessels are formed in areas of the holes, or is coated by a water-repellent material except for the areas corresponding to the reaction vessels so that the reaction vessels are formed in areas surrounded by the water-repellent material.

As the glycan binding protein, a lectin or a glycan recognition antibody belonging to an IgM class can be used.

The substrate can be one in which the glycan binding proteins are arranged and immobilized in a predetermined pattern in accordance with the type thereof.

An antibody to a portion other than the glycan of the complex carbohydrate can be arranged and immobilized together with the glycan binding protein on the substrate.

The analyzer of the present invention can have a memory means for storing the fluorescent intensity measured by the fluorescent intensity measurement means on every position of arranging the glycan binding proteins corresponding to the glycan to be detected or the complex carbohydrate to be detected that are used.

The analyzer of the present can have a memory means for storing the measured fluorescent intensity divided by steps on every position of arranging the glycan binding protein.

An analyzer of the present can have an indication means for indicating the fluorescent intensity divided stepwise on every type of each of the glycan binding proteins.

The substrate can be one in which multiple types of identical glycan binding proteins are arranged and immobilized on every type thereof.

An analyzer of the present can have a calculation and memory means for calculating and storing an average value of the fluorescent intensity measured for identical glycan binding proteins.

An analyzer of the present can have a memory means for storing stepwise average values of fluorescent intensities measured for identical glycan binding proteins.

An analyzer of the present can have an indication means for indicating stepwise the fluorescent intensities being divided on every type of the glycan binding proteins.

The memory means can store the fluorescent intensity information for known glycans or complex carbohydrates.

An analyzer of the present can have a selection means for matching the fluorescent intensity information for a glycan or a glycoside protein as a target of analysis to the fluorescent intensity information for known glycans or complex carbohydrates, and selecting an identical or approximate glycan or complex carbohydrate.

Effect of the Invention

According to the analyzer of the invention, the cleaning and removing operation for the probe solution which resulted a significant problem in accurate analysis for the information on the interaction between a glycan binding protein such as a lectin and a glycan in an equilibrium state is not more necessary, and weak interaction that may be flushed off upon cleaning in the existent method can also be detected.

That is, means for observing the interaction between the glycan binding protein and the glycan in the equilibrium state as it is has been put to practical use for the first time. By the use of the apparatus, not the presence or absence (0 to 1) for the binding such as in the existent lectin plotting but information for an intermediate portion, that is, information for the binding intensity can be obtained (for example, as 0 to 6 stages). This means that the amount of information in the interaction between the glycan binding protein and the glycan by the number of n chain is increased outstandingly from existent $2^n$ modes to $6^n$ modes. The technique will provide a significant contribution to the development in the glycan structural analysis, as well as other various relevant fields of glycan technology by further increasing the density and improving the accuracy in the feature. Further, by manufacturing arrays for the analysis of interaction between glycan binding protein and glycan directed to various application uses, thereby analyzing, for example, the glycans of the glycoside proteins and the quantitative ratio thereof in living specimens such as stock solutions or dilute solutions of bloods, body fluids, tissue extracts, etc., they can be utilized to diagnosis and judgment of various diseases, as well as applied widely to the quality control of glycoside protein formulations.

BEST MODE FOR PRACTICING THE INVENTION

Figure 1:
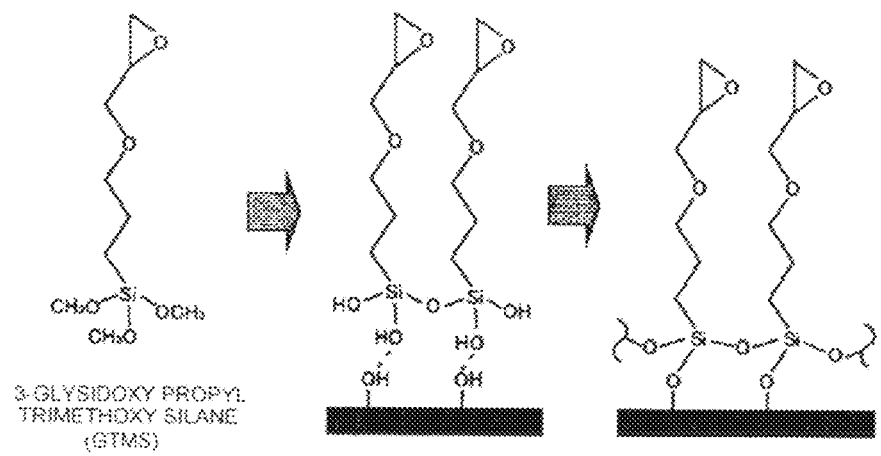
FIG. 1 is a schematic view showing the reaction process of GTMS to a glass surface.

An analyzer of the present invention is for fluorescence-labeling a glycan to be detected or a complex carbohydrate to be detected with or without purification, measuring the binding state of the glycan or the complex carbohydrate and a protein thereby, and analyzing the glycan to be detected or the complex carbohydrate to be detected, or a specimen containing the same.

The analyzer includes a substrate, fluorescent labeling excitation means and a fluorescent intensity measurement means.

The substrate comprises a rectangle photoconductive base plate coated by a compound containing an active group to fix protein by an amino group thereof, one and more open-topped reaction vessel formed on a surface of the base plate, and plural spots of glycan binding proteins arranged in a matrix and immobilized on the surface of the base plate in the reaction vessel.

The fluorescent labeling excitation means which excites fluorescent label by generating evanescent-waves on the surface of the substrate comprises a pair of optical fibers arranged toward the both side end faces of the right and left of the substrate to introduce a light thereinto.

The fluorescent intensity measurement means for measuring the intensity of fluorescence generated by the fluorescent labeling excitation means on every spots of arranging the glycan binding protein.

While the glycan or the complex carbohydrate as a target for analysis by the apparatus according to the invention has no particular restriction, the chain includes, for example, glycoside protein type glycan (N-binding type glycan and O-binding type glycan), glucolipid type glycan, glycosamino glycane type glycan, and polysaccharide-derived oligo saccharide chain. Further, there are mentioned, for example, (1) N-binding type glycan comprising high mannose type-hybrid type-composite type as N-binding type glycan, (2) O-binding type glycan comprising mutin type (O-GalNAc) .O-Fuc type.O-Man type.O-Glc type as the O-binding type glycan, (3) gangrio series.glovo series.facto.neolacto series glycans for glycan lipid series glycan, (4) hyaluronic acid-.karatan sulfuric acid.hepalin.heparan sulfuric acid.chondroitin sulfuric acid.dermatan sulfuric acid as glucosamino glycan series glycan, (5) oligosaccharides derived from chitin, cellulose, curdlan, laminarin, dextran, starch, glycogen, alabino galactan, arginic acid, fructan, fucoidan, or xylane as oligosaccharide-derived oligoglycans.

Other glycans include, for example, M3, M5A, Hybrid (monoagalacto, bisect), NA1, NA1 ($\alpha$1-6Fuc), NA2 (monoagalacto), NA2 (monoagalacto, bisect), NA2, NA2 ($\alpha$1-6Fuc), A2, NA2 (bisect), NA3, NA3 ($\alpha$1-6Fuc), NA4, NA4 ($\alpha$1-6Fuc), NA5 (pentaagalacto, bisect), Lactose, GA2, GA1, GM3-NeuAc, GM3-NeuGc, GM1, GM2, GD1a, DG1b, GD3, Gb3, Gb4, Forssman, LNnT, LNT, Galili pentasaccharide, B-hexasaccharide, LNFP-I, LNFP-II(Le$^a$), LNFP-III (Le$^x$), LNFP-II(Le$^b$), A-hexaccharide, A-heptasaccharide, B-pentasaccharide, 6'-Sialyl lactose, pLNH, $\beta$ GalLac, $\beta$Gal$_2$Lac, LN3, GN3, GN4, maltotriose, Sialyl Le$^x$.

Further, in the invention, the complex carbohydrate is a collective name of in-vivo polymers having glycans. The complex carbohydrate of the invention includes glycoprotein (also including glycopeptide), proteoglycan, and glycolipid.

As the glycan binding protein immobilized on the substrate, lectin is preferred for example and the lectin includes lectins belonging to various molecule families obtained, for example, from animals and plants, fungus, bacteria, and virus, that is, lysine B chain-related "R type lectin" distributed in all biological fields including bacteria, "calnexin, calreticulin" present generally in eukaryotes and concerning folding of glycoside protein, calcium demanding "C-type lectin" present generally in multicellular animals and containing may typical lectins, "galectin" distributed generally in the animal field and showing specificity to galactose, "leguminous lectin" forming a large family in plant leguminous, and "L-lectin" having structural similarity therewith and concerning animal intracell transportation, mannose 6-phosphate binding "P-lectin" concerning intracell transportation of lysosomal enzyme, "annexin" binding to acidic glycan including glycosamino glycan, and "I-type lectin" belonging to immune globrin superfamily and including "siglec".

Other lectins include, for example, ACA (*Amaranthus caudatus* L.), BPL (*Bauhinia purpurea* L.), ConA (*Canavalia ensiformis*), DBA (*Dolichos biflorus*), DSA (*Datura stramonium*), ECA (*Erythrina cristagalli*), EEL (*Euonymus europaeus*), GNA (*Galanthus nivalis*), GSL I (*Griffonia simplicifolia*), GSL II (*Griffonia simplicifolia*), HHL (*Hippeastrum* hybridum), Jacalin (*Artocarpus integrifolia*), LBA (*Phaseolus lunatus*), LCA (*Lens culinaris*), LEL (*Lycopersicon esculentum*), LTL (*Lotus tetragonolobus*), MPA (*Maclura pomifera*), NPA (*Narcissus pseudo-narcissus*), PHA-E (*Phaseolus vulgaris*, erythroagglutinating isoform of PHA), PHA-L (Phytohemagglutinin (*Phaseolus vulgaris*, leocoagglutinating isoform of PHA)), PNA (*Arachis hypogaea*), PSA (*Pisum sativum* L.), PTL-I (*Psophocarpus tetragonolobus*), PTL-II (*Psophocarpus tetragonolobus*), PWM (*Phytolacca americana* L.), RCA120 (*Ricinus communis*), SBA (*Glycine max*), SJA (*Sophora japonica*), SNA (*Sambucus nigra*), SSA (*Sambucus sieboldiana*), STL (*Solanum tuberosum*), TJA-I (*Trichosanthes japonica*), TJA-II (*Trichosanthes japonica*), UDA (*Urtica dioca*), UEA I (*Ulex europaeus* L.), VFA (*Vicia fava*), VVA (*Vicia villosa*), WFA (*Wisteria floribunda*), WGA (*Triticum vulgare*).

Further, lectins immobilized on the substrate include those modified from the lectins described above for the physical property, binding specificity and affinity by the method, for example, of introducing site specific mutation, or chemical modification. The lectin referred to in the specification also includes such lectin variants. Further, the present invention concerns an apparatus for enabling analysis of a relatively weak interaction between a glycan and a protein compared with the antigen-antibody reaction and the glycan binding protein of weak interaction is not restricted to the lectin. That is, glycan recognition antibody generally having weak interaction (for example, glycan recognition antibody classified to the IgM class) is also included.

The substrate in the invention comprises a rectangle photoconductive base plate coated by a compound containing an active group to fix protein by an amino group thereof, one and more open-topped reaction vessel formed on a surface of the base plate, and plural spots of glycan binding proteins arranged in a matrix and immobilized on the surface of the base plate in the reaction vessel.

The photoconductive base plate may be any base plate having a photoconductivity and capable of generating evanescent waves on the surface thereof by the light irradiation means of the analyzer according to the invention and includes, for example, glass, quartz glass, and synthesis quartz glass, but it is not restricted to them.

Further, the compound coating the base plate preferably has an epoxy group as an active group, it is not restricted thereto but may be a substrate on which a glycan binding protein such as lectin is immobilized on the substrate coated with vinyl sulfonic group, active ester group, aldehyde group, carboxyl group, amino group, thiol group, isothiocyanate group, etc.

The compound having the epoxy group as the active group includes, preferably, 3-glysidoxy propyl trimethoxy silane (GTMS) but is not restricted thereto. Other examples include, for example, 2-(3,4 epoxy cyclohexyl)ethyl trimethoxysilane, 3-glysidoxy propyl methyl diethoxy silane, 3-glysidoxy propyl triethoxy silane, or a silane coupling compound having a plurality of epoxy groups at the top ends of branched spacers and, preferably, compounds, for example, containing polyethylene glycol, protein, biotin.avidin, etc.

The substrate used for the analysis of the glycan or the complex carbohydrate of the invention is a substrate in which multiple types of glycan binding proteins such as lectins are arranged and immobilized on the surface thereof and can be manufactured, for example, by the following method.

Description is to be made to an example of using lectin as a glycan binding protein.

At first, a compound having an epoxy group as an active group is coated to a slide glass as a rectangle photoconductive base plate.

For example, in a case of using GTMS as a compound having the epoxy group as the active group, it can be conducted by the method described in the example to be described later. Specifically, a slide glass is dipped in a 10% KOH/MeOH solution, left for one hour in a state of being shaken together with the vessel thereby treating the glass surface, which is cleaned with a sufficient amount of pure water (milli Q water) and then dried in an oven at 60° C. Then, the slide glass is dipped into a 2% GTMS acetone solution, and reaction is taken place for one hour while being shaken together with a vessel under shielding of light. The alkoxy silyl group of GTMS is transformed into a silanol group by hydrolysis with water, the silanol group is instable and partially bonded into the state of an oligomer by change with time and, successively, adsorbed by way of hydrogen binding to the glass surface. After the reaction, the slide glass is dried in an oven at 110° C. for 8 hours. By the drying treatment, dewatering condensation reaction with silanol groups on the glass surface occurs to form a strong covalent bond. FIG. 1 shows a series of GTMS coating method.

Then, a lectin is spotted to a slide glass coated with the compound having the epoxy group as the active group and can be immobilized by reaction utilizing the amino group of the lectin. In the invention, multiple types of lectins are spotted on one identical slide glass.

Further, in this case, the plurality types of lectins are desirably arranged and immobilized by spotting in a predetermined pattern according to the types thereof. Thus, the judgment for the difference or judgment for the similarity between the glycans or the complex carbohydrates of the specimens or for known glycans or complex carbohydrates can be conducted easily.

In the manufacture of the array, a commercially available pin type spotter for use in manufacture of DNA microarrays or a non-contact type ink jet spotter can be utilized. After spotting the lectins, unbonded lectins can be removed by cleaning with a Tween 20-containing PBS solution (PBST).

Figure 2:
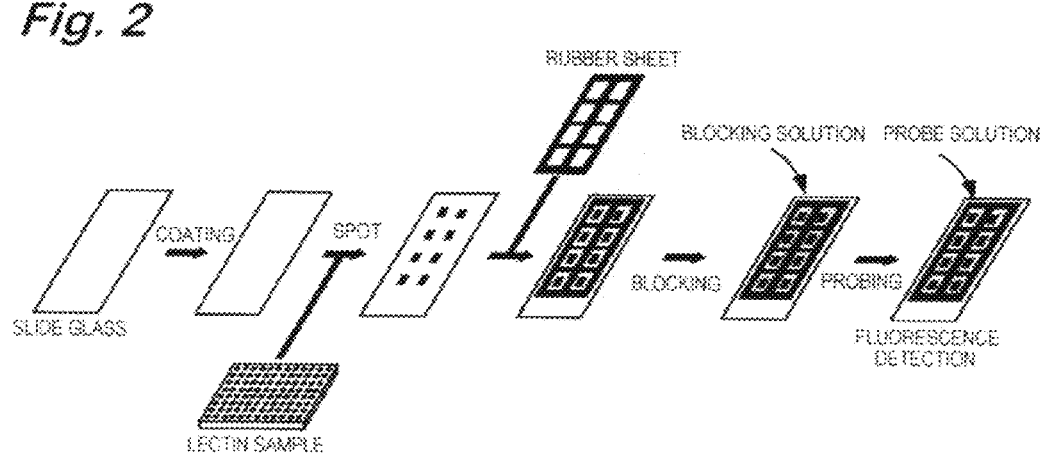
FIG. 2 is a view showing the outline for a method of manufacturing a substrate for use in analysis of a glycan or complex carbohydrate of the invention.

On the surface of the base plate to which the lectins are immobilized, a plurality of open-topped reaction vessels are formed (refer to FIG. 2).

More preferably, a plurality of reaction vessels are formed by bonding rubber having a plurality of holes on the base plate.

As an example, a 8-hole silicon rubber designed and developed by the present inventors is bonded to a predetermined position relative to a slide glass where a protein that exhibits interaction with the glycan to manufacture eight reaction vessels as described in the example. In the 8-hole rubber, eight rectangular holes are formed regularly and a fluorescence labeling glycan probe solution can be filled accurately to the periphery of the spots by bringing it in close contact with the slight glass on an adjuster used exclusively therefor. By filling the reaction vessel with the fluorescent labeled probe solution, contact with the protein that exhibits interaction with the glycan can be conducted smoothly. Further, the reaction vessel is preferably made by plurality and, more preferably, 12 or 16 reaction vessels are arranged each at an interval identical with the standard of the commercially available 96, 384 well plates.

Further, the material for forming the reaction vessel is not restricted to the silicone rubber but, for example, it is possible to form the reaction site by applying water repellent coating to a non-spot region of the glass surface, or utilizing the vessel of a 96 well plate standard.

On the other hand, in the substrate of the invention, it is preferred to arrange and immobilize a plurality of lectins of an identical type. This enables to calculate an average value for the fluorescent intensity based on the interaction of the glycan or the complex carbohydrate to be detected to the lectins of identical type thereby enabling to mitigate the measuring error, for example, due to scatting of measured signal intensity derived, for example, from defects of size and the shape of spots, difference for the amount of immobilization of lectins derived from inhomogeneity of the substrate, or the number of leveled probe molecules bonded to the spots, inhomogeneity of the excitation light, or electrical nozzles in detection elements.

Further, in the substrate of the invention, multiple types of glycan binding proteins such as lectins are arranged and immobilized and, further, antibodies to the protein moieties of the glycoside proteins can be arranged and immobilized further (manufacture of hybrid array) upon analysis of glycoside proteins. According to the substrate, analysis for the glycan portion of the glycoside protein and analysis for the protein portion can be conducted simultaneously. This can simply distinguish those of identical glycan although different in the protein or those of identical protein although different in the glycan.

Figure 3:
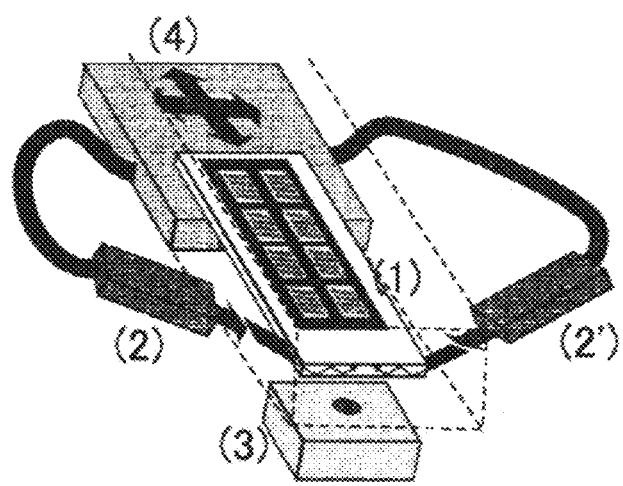
FIG. 3 is a view showing an example of an analyzer for a glycan or a complex carbohydrate of the invention.

FIG. 3 is a view showing an example of an analyzer according to the invention.

The apparatus has a substrate (1) comprising a photoconductive material in which multiple types of glycan binding proteins such as lectins are arranged and immobilized, means (2), (2') for introducing light to the end face on the side of the substrate and generating evanescent waves to the surface of the substrate thereby exciting the fluorescent labeling, and fluorescent intensity measurement means (3) for measuring the intensity of the fluorescence generated by the means described above on every position for arranging the glycan binding proteins, in which the substrate (1) is mounted detachably on a substrate mounting means (4), and the substrate mounting means preferably has a frame for guiding the fluorescence generated on the substrate to the fluorescent intensity measurement means without shielding the fluorescence.

The fluorescence labeling excitation means (2), (2') which excites fluorescent label by generating evanescent-waves on the surface of the substrate comprises a pair of optical fibers arranged toward the both side end faces of the right and left of the substrate (1) to introduce a light into the substrate (1).

The evanescent waves are generated upon total reflection of a light at the boundary between substances, and the incident angle for causing total reflection is different depending on the substance and the material. In the invention, for adjusting the incident angle so as to conform various materials of substrates, the fluorescent labeling excitation means (2), (2') are provided such that the introduction angle of the light to the end face of the side of the substrate can be adjusted.

Further, the fluorescence labeling excitation means comprises a pair of optical fibers arranged toward the both side end faces of the right and left of the substrate.

Thereby, even in a case where the number of row of the glycan binding proteins is large, it can introduce excitation lights from the both side end faces of the right and left of the substrate at same time, so that uniform evanescent waves can be generated on the surface of the substrate.

As the type of the light introduced by the fluorescence-labeling excitation means (2), (2'), to the end face of the substrate, pulse or continuous monochromatic light obtained from laser, LD, or LED, white light obtained from a metal hydride lamp, xenon lamp or the like as it is, or a light cut out therefrom by an optical filter to an optional wavelength range can be used for example.

The fluorescent intensity measurement means (3) has no particular restriction, and a charge coupled device (CCD) camera, image intensifier charge coupled device (ICCD) camera, cooled CCD camera, photomultiplier (PMT), etc. can also be used.

In a case of measuring the intensity of fluorescence generated above the substrate (1) by the excitation of evanescent waves, scanning is conducted by displacing the substrate mounting means (4) on the fluorescent intensity measurement means (3) to move the entire surface of a substrate for immobilizing glycan binding protein, for example, in directions XY, in which scanning may be conducted also by moving the fluorescent intensity measurement means (3) while fixing the substrate (1).

Description is to be made specially to a case of analyzing glycans to be detected or complex carbohydrates to be detected by using the analyzer described above of the invention.

In the invention, at first, a substrate (1) on which glycan binding proteins such as a plural types of lectins are arranged and immobilized is mounted on the substrate mounting means (4), a specimen containing fluorescence-labeled glycans to be detected or complex carbohydrates to be detected is introduced on the substrate (1), and each of the glycan binding proteins on the substrate (1) and the fluorescence-labeled glycans to be detected or complex carbohydrates to be detected are contacted with each other.

In the invention, the fluorescence labeling agent of the glycan to be detected or the complex carbohydrate to be detected includes 2-aminopyridine, Cy3, Cy3.5, Cy5, tetramethylrhodamine, and various fluorescence dyes having fluorescein skeletons, Alexa series fluorescence dyes manufactured by Molecular Probes Co., and quantum dot fluorescence dyes but it is not restricted to them so long as it is a substance having a property of fluorescence labeling the glycan.

The glycan to be detected or the complex carbohydrate to be detected can be fluorescence-labeled directly or indirectly. By binding a glycan to be detected and a previously fluorescence labeled glycan binding protein, the glycan to be detected can be fluorescence-labeled indirectly.

Further, by binding a previously fluorescence-labeled protein which is a protein binding to a portion other than the glycan of the complex carbohydrate to be detected (for example, an antibody showing interaction with a portion other than the glycan of the complex carbohydrate to be detected) and a complex carbohydrate to be detected, the complex carbohydrate to be detected can be fluorescence-labeled indirectly.

Further, the complex carbohydrate can be fluorescence-labeled indirectly also by binding a previously fluorescence-labeled glycan binding protein and a complex carbohydrate to be detected (in this case, in the glycans of the complex carbohydrate to be detected, glycans other than the glycan bonded with the glycan binding protein are bonded to the substrate).

For example, by acting a previously fluorescence-labeled antibody that exhibits an interaction with a portion other than the glycan of a target complex carbohydrate on a crude specimen containing a target complex carbohydrate specimen such as blood, body fluid, living body extracts, food ingredients, etc., the target complex carbohydrate can be selectively fluorescence-labeled without separation or purification from the crude specimens. Further, by bringing a crude specimen acted with a previously fluorescence-labeled antibody into contact with a substrate on which glycan binding proteins such as lectins are immobilized for instance, only the glycan information of the target complex carbohydrate can be observed selectively.

In a case of using the apparatus of the invention, a light is then introduced from the fluorescence labeling excitation means (2), (2') to the end face on the side of the substrate without cleaning the substrate (1) to generate evanescent waves on the surface of the substrate and excite fluorescent labeling groups of the glycan or the complex carbohydrate to be detected.

In the evanescent excitation system, it has been known that a weak light referred to as an evanescent light exudes within a range of 200 to 300 nm from the boundary (about one-half excitation wavelength) upon totally reflecting the fluorescent light in the inside of glass.

When the fluorescence labeling groups are excited by utilizing the evanescent light in a state of contacting a solution containing a glycan or a complex carbohydrate labeled with a fluorescent substance on a slide glass, probe molecules near the boundary contributing to the binding reaction can be observed selectively without scarcely exciting fluorescence-labeled molecules under Brownian motion, that is, molecules not contributing to the binding reaction.

For example, since the interaction between a lectin or a glycan recognition antibody such as of an IgM class immobilized to the substrate and a glycan to be detected or a complex carbohydrate to be detected is weak compared, for example, with the interaction between proteins well known generally, when the operation of removing and cleaning the probe solution is conducted, dissociation reaction proceeds between the glycan binding protein and the glycan to be detected or the complex carbohydrate to be detected to sometimes result in a case that no accurate interaction information under an equilibrium state can be obtained.

The present inventors have solved the problem described above by exciting the fluorescence labeling groups by the evanescence waves and measuring the intensity of fluorescence without cleaning the probe solution. Further, since scanning can be conducted not by way of the cleaning, the change with time of the interaction can be traced just after the addition of the probe by conducting scanning continuously on every predetermined time interval and it can be easily judged as to whether the interaction reaction between each of the glycan binding proteins immobilized on an identical glass and the probe reaches an equilibrium state or not.

The fluorescence generated by the excitation of the evanescence waves is measured for the fluorescent intensity thereof by the fluorescent intensity measurement means (3) on every position for arranging each of the glycan binding proteins on the substrate (in a case of arranging and immobilizing multiple types of lectins on a substrate, the fluorescent intensity is measured on the position for arranging each of the lectins, that is, on every types of lectin). For example, by comparing the fluorescent intensity of the glycan to be detected to each of lectins and the fluorescent intensity of each of the known glycans to each of lectins measured in the same manner, difference, similarity, non-similarity, etc. thereof can be judged.

In this case, when a substrate is scanned, for example, on an ICCD camera as fluorescent intensity means and the fluorescent intensity to each of lectins is displayed as images, comparison is made more easily.

The invention provides useful means as a glycan profiler for conducting the glycan structural analysis rapidly and conveniently. For example, a profiling method described in Protein, Nucleic Acid, Enzyme, in August 2003, special Vol. 48, No. 11 is applicable to the means described above.

That is, the measured values for the fluorescent intensity in the apparatus of the invention are used for the glycan structural analysis by conducting information processing using a computer. Accordingly, the apparatus of the invention includes such an information processing system by the computer. The structure of the glycan to be detected can be identified in a case where the glycan to be detected has a known structure. Also in a case where the glycan detected has an unknown structure, it is possible to predict a characteristic structure present in the glycan to be detected (for example, α2-3 sialic acid, α2-6 sialic acid.α1-3 galactose.α1-3 fucose.α1-6 fucose.sulfated bisect N-acetyl glucosamine, etc.) or point out the similarity with a glycan of known structure.

This means is a system of automatically displaying a glycan structure when setting, to an apparatus, a substrate in which multiple types of glycan binding proteins, for example, multiple types of lectins which are brought into contact with a fluorescence-labeled glycan to be detected and exhibit interaction with the glycan or glycan to be detected.

In the apparatus having such a system, a step of bringing a fluorescence-labeled glycan to be detected to a substrate on which various proteins exhibiting interaction with the glycan are immobilized respectively can be automated. That is, by introducing a micro flow channel system to a reaction vessel on a substrate, and controlling the type, concentration, and flow rate of a solution to be sent into the flow channel, the step of blocking or cleaning and eliminating a blocking solution, and a contact step of the fluorescence-labeled glycan solution can be controlled uniformly. Since data of higher reliability can be obtained by using the methods, they are extremely useful.

Further, in a case of estimating a partial glycan structure of a glycan to be detected by the apparatus according to the invention, data of higher reliability can be obtained by using enzymatic digestion by glycoside hydrolase. For example, in a case of judging whether sialic acid is contained in the non-termination partial glycan structure of a glycan to be detected or not and, further, whether the binding site is α 2-3 or α 2-6 in a case where it is contained, this can be conducted easily by digesting the glycan to be detected with a highly specific sialidase (for example, α 2-3 neuraminidase cleaves only α 2-3 sialic acid, and sialidase derived from *Arthrobacter ureafaciens* cleaves α 2-6 sialic acid more preferably than α 2-3 sialic acid) and examining the presence or absence for the change of the profile before and after the reaction. Further, by sequentially reacting plural types of glycoside hydrolase, partial glycan structures can be estimated in a wider range. By preparing eight reaction vessels on a glass, it is possible to profile eight types of enzyme digestion reaction products simultaneously and this further facilitates estimation for the glycan structure.

The glycoside hydrolase that can be used for the estimation of the partial glycan structure by enzymatic digestion includes, in addition, β-galactosidase derived from Jack Bean, α (1-3,4,6)-galactosidase derived from Green Coffee Bean, β-N-acetylhexosaminidase derived from *Streptococcus pneumoniae*, α-N-acetyl galactosaminidase derived from chicken liver, α(1-2,3,6)manosidase derived from Jack Bean, β mannosidase derived from *Helix pomatia*, α fucosidase derived from bovine kidney, α 1,2-L-fucosidase derived from *Corynebacterium* sp., β 1,2-xylosidase derived from *Xanthomonas* sp., and recombinants for all of them.

In a case of estimating the presence of N-binding type and O-binding type glycans in the glycoprotein to be detected and the structure thereof, the reliability of the data for the structural estimation is improved by using an end type glycoside hydrolase together. The end type glycoside hydrolase usable in this case includes, for example, end glycosidase H derived from *Streptomyces plicatus*, PNGase F derived from *Flavobacterium meningosepticum*, O-glycanase derived from *Streptococcus pneumoniae*, endo glycosidase F1 derived from *Chryseobacterium meningosepticum*, and all of recombinants thereof.

Figure 4:
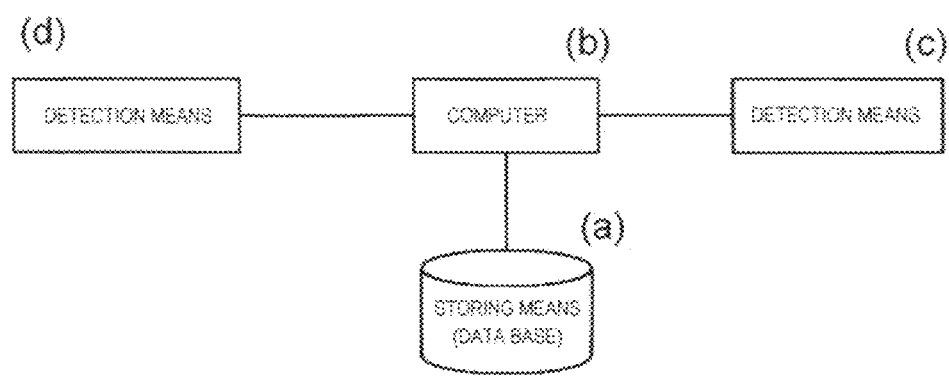
FIG. 4 is a view showing an example of an information processing system of the invention.

FIG. 4 shows an example of an information processing system of the invention.

The system includes at least the following means (a) to (c).

(a) Memory means (database) for classifying the fluorescent intensity data on every position for arranging glycan binding proteins, for example, lectins (on every type of lectin) measured by using the analyzer of the invention for each of glycans or complex carbohydrates of known structures and patterning and storing the interaction to various glycan binding proteins while classifying on every 3 steps or 6 steps, for example, strong, medium, or weak.

(b) A computer including calculation means for corresponding the fluorescent intensity measuring data on every position for arranging various glycan binding proteins on a substrate measured by using the analyzer of the invention for the glycan to be detected or the complex carbohydrate to be detected, and data stored in the memory means (a), and selecting one or a plurality of glycans or complex carbohydrate of known structures to which the measured data or the pattern is identical or similar.

(c) Display means for displaying the result of selection

In the following descriptions, the measured data or the patterned data are sometimes referred to collectively as fluorescent intensity information.

Figure 5:
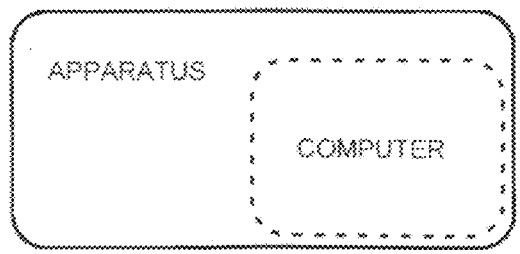
FIG. 5 is a view showing an example of a system accommodating a database to the outside of a computer.
Figure 6:
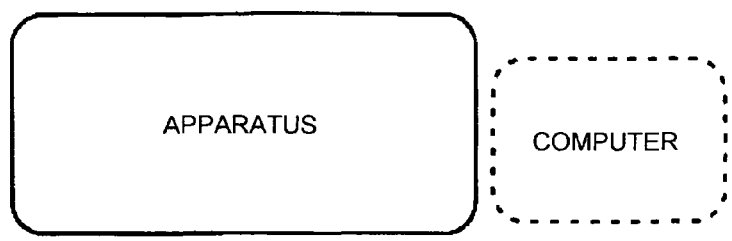
FIG. 6 is a view showing an example of a system accommodating a database to the inside of a computer.

The data base in this system may include both a case where it is present outside of a computer as shown in FIG. 5 and a case where it is present in the inside of the computer as shown in FIG. 6. Further, by utilizing the data base, also in a case where the number of the types of the glycan binding proteins measured for the fluorescent intensity is limited, various types of glycans can be discriminated. For example, in a case of recognition by dividing measured signal intensity into 6 steps, when 10 types of lectins of sufficiently different in the property are utilized, the type of the recognizable glycans are theoretically $10^6=60,466,176$, by which almost glycan structures actually present in the natural world can be distinguished.

Figure 7:
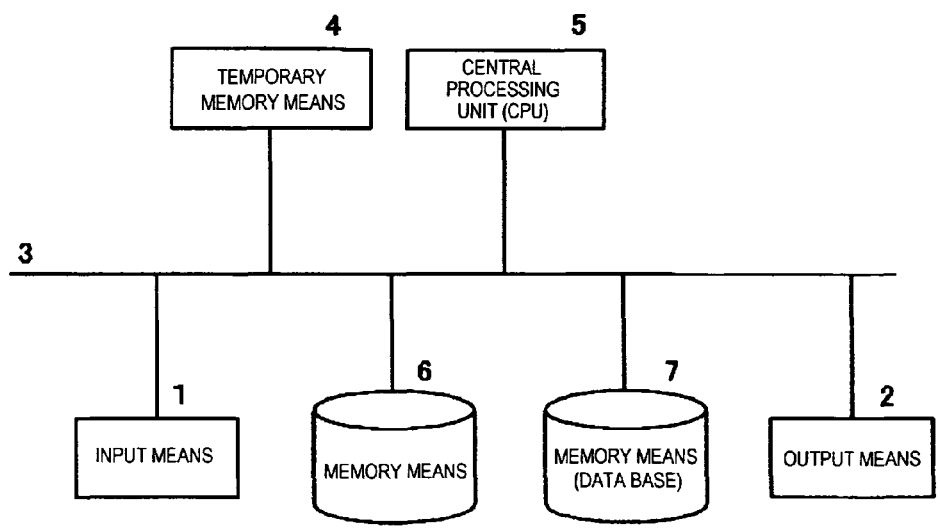
FIG. 7 is a view showing an example of a constitutional view of a computer in the system of the invention.

FIG. 7 shows an example for the constitutional view of a computer in the system of the invention. Input means 1 and output means 2 are connected to a bus line 3. A temporary memory means 4 temporarily stores inputted information, calculated information, etc. A central processing unit (CPU) 5 receives instructions from the program of the invention and conducts various calculations. A memory means (data base) 7 stores fluorescent intensity data for various glycan binding proteins on known glycans or complex carbohydrates, or patterned information like those described above.

In addition, information on the binding property between the glycans or the complex carbohydrates and the glycan binding proteins obtained by other experimental systems may also be stored.

The memory means 6 accommodates various programs including a program for executing the processing of the invention. The program for executing the processing of the invention at least contains a program 61 for corresponding the inputted fluorescent intensity data of various glycan binding proteins for glycans or complex carbohydrates or patterned information thereof to similar fluorescent intensity information of known glycans or complex carbohydrates stored in the data base or the patterned information thereof, and selecting one or a plurality of glycans of known structures having identical or similar data or the pattern (information of glycans of known structures stored in the data base), a display program 62, and a program 63 for controlling them.

As apparent from the foregoings, in the process for corresponding the fluorescent intensity data with the known glycans or complex carbohydrates and the patterned information thereof, values for the data may be compared with each other. The program 61 may be incorporated with a function of comparing the values for the inputted fluorescent intensity data with the values for the information of known glycans or complex carbohydrates stored in the data base and selecting one or a plurality of glycans of known structure in view of the close relation between the values.

Figure 8:
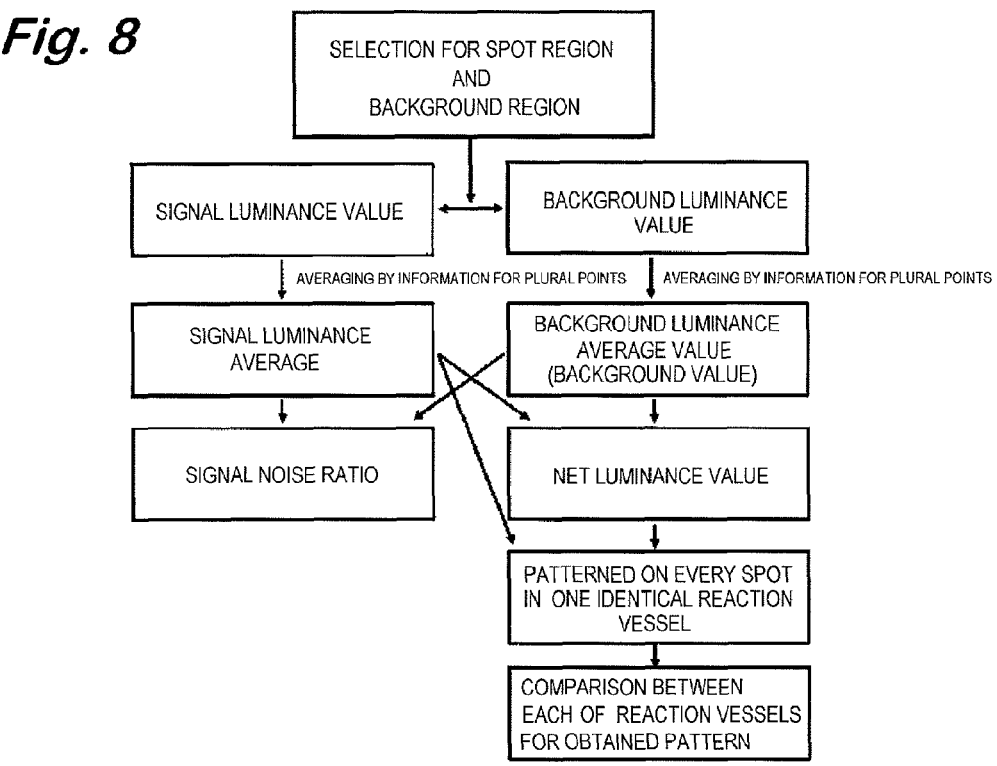
FIG. 8 is a view showing a flowchart for a patterning treatment of a program used in the analyzer of the invention.
Figure 9A:
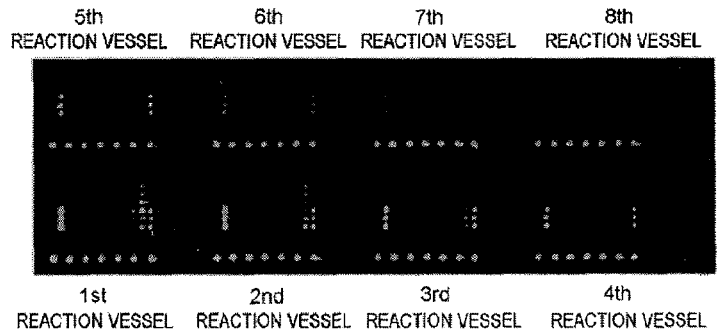
FIGS. 9a-9i are views showing a patterned information showing the result processed by the program in FIG. 8.
Figure 9B:
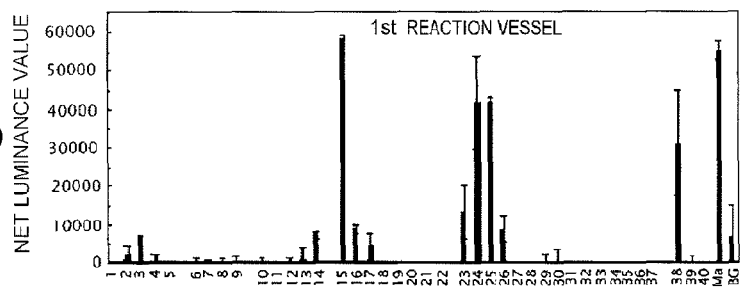
Figure 9C:
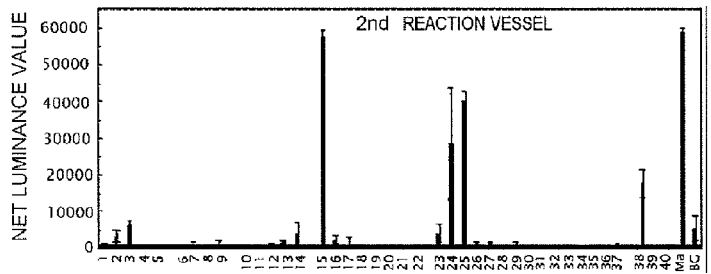
Figure 9D:
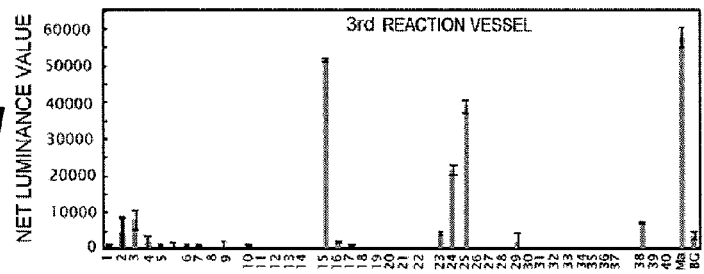
Figure 9E:
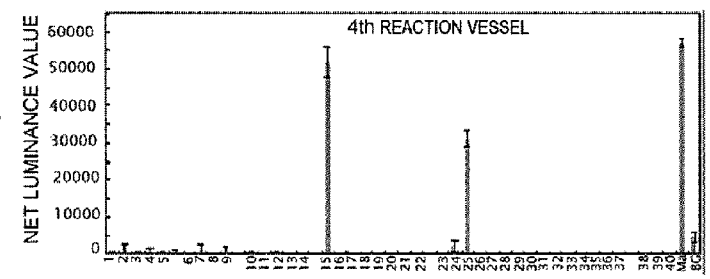
Figure 9F:
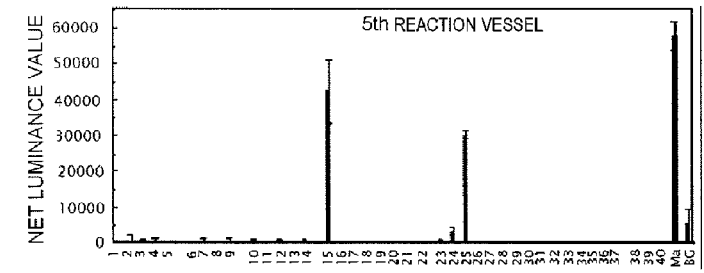
Figure 9G:
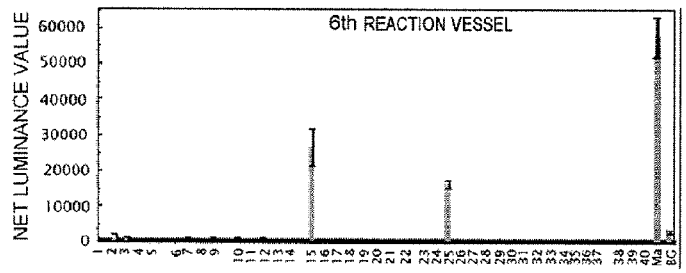
Figure 9H:
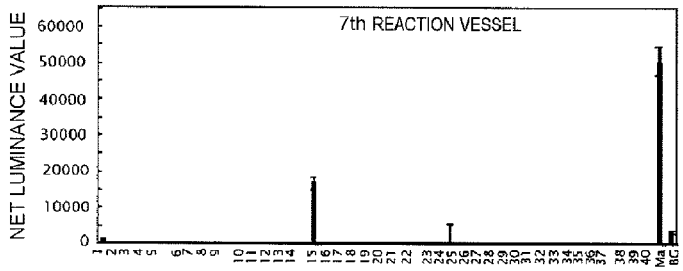
Figure 9I:
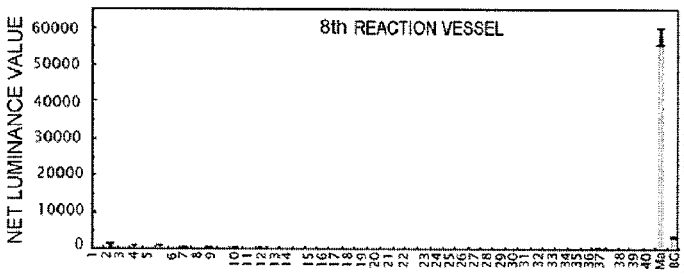

Program 62 (FIG. 8) executes display for average fluorescent intensity data for each spot obtained for the glycan to be detected or the complex carbohydrate to be detected, signal noise ratio (S/N ratio) and fluctuation thereof, standard deviation, net luminance value calculated from the fluorescent intensity and patterned information obtained by pattering the same (FIGS. 9a-9i), information for the selected glycan of known structure, etc. Upon patterning, the information for the interaction can be normalized by using an appropriate internal standard.

In the invention, the programs described above can be collected in one program.

In the analyzer of the invention, the lectin immobilizing substrate (1) may be set in plurality to the analyzer, automatically transferred to the fluorescent intensity measuring section successively, the fluorescence labeling excitation means (3) is actuated to conduct scanning, and the obtained fluorescent intensity data may be automatically inputted to the computer. The inputted data may be stored in the memory means or the temporary memory means of the computer. Further, the fluorescent intensity data or the patterned information formed by patterning the same are preferably stored together with the information derived from the glycan or complex carbohydrate to be detected in the data base. Further, also by sequential accumulation of the structural information as the glycan structures have been found, it is possible to construct information data base for the analysis of the glycan structures based on the binding state of the glycans or the complex carbohydrates and various glycan binding proteins, having a large scale and of high utility which can not be present so far.

According to the invention, the calculation means such as the central processing unit (CPU) receives instructions from the program 62 stored in the memory means, reads out the fluorescent intensity information stored in the memory means or the temporary memory means to display the fluorescent intensity information. However, by using fluorescent intensity generated from a specified glycan binding protein specimen spots (internal standard spots) showing interaction with glycans previously investigated sufficiently for the property as the standard, and values amended for the luminance for each spot can be displayed. The internal standard spot may be present in plurality.

As an example of the processing flow, the fluorescent intensity information inputted then is corresponded to the fluorescent intensity information of various glycans to various glycan binding proteins stored in the data base, and one or a plurality of glycans of known structures of identical patterns are selected. In the processing step, the calculation means such as the central processing unit (CPU) receives the instruction from the program 61 in the memory means, corresponds the fluorescent intensity information stored in the memory means or the temporary memory means and the fluorescent intensity information for the glycans or complex carbohydrates for the known glycans or complex carbohydrates stored in the data base, and selects one or a plurality of glycans of known structures identical or similar in the pattern of information. The selected information for the glycans of known structures can be stored in the memory means or the temporary memory means of the computer.

In a case where the data base is present outside of the computer, the calculation means such as the central processing unit (CPU) receives the instruction from the program 61 in the memory means, inputs the fluorescent intensity information for the known glycans or complex carbohydrates stored in the data base into the computer, reads out the fluorescent intensity information stored in the memory means or the temporary memory means in the computer, corresponds the respective fluorescent intensity information, and selects one or a plurality of glycans of known structures identical in the pattern of information.

As one example of the processing flow, the result of selection is then displayed by the display means.

In the processing step, the calculation means such as the central processing unit (CPU) receives the instruction from the program 62 in the memory means, and reads out and displays the information of the glycans of known structures stored in the memory means or the temporary memory means.

The invention is useful as a method of rapidly and conveniently examining the state of the glycan modification of an aimed protein from a mixture of different complex carbohydrates, for which application use may be considered in such fields as recognition for the situation of diagnosis or therapy by observing the state of the glycan modification of the aimed protein without purifying the mixed solution of various ingredients such as a stock solution or dilute solution of bloods, body fluids, living body extract ingredients, food ingredients, etc.

All the prior art documents cited in the present specification are incorporated by reference to the present specification.

Figure 10:
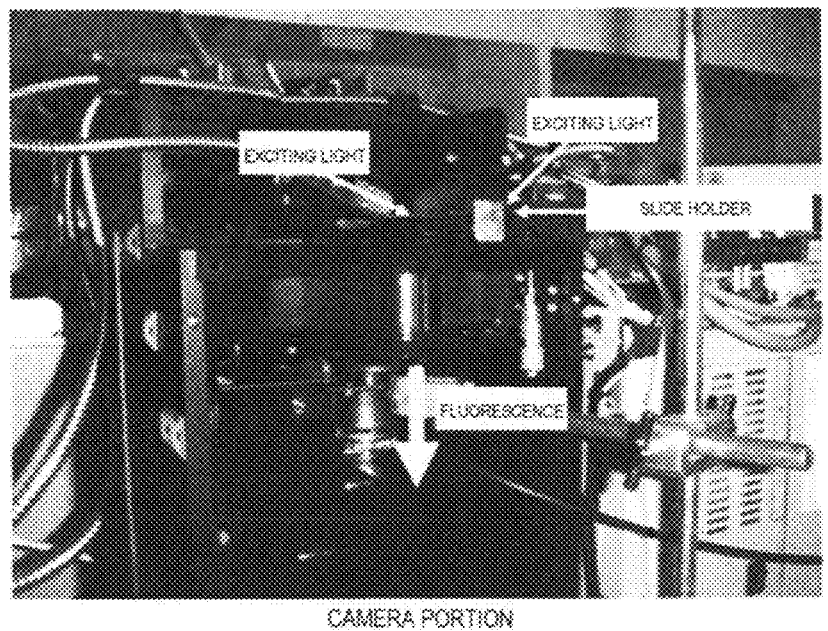
FIG. 10 is a view showing an example for the appearance of an analyzer for a glycan or a complex carbohydrate of the invention.

Examples of the invention are to be shown below. In the examples, glycans were actually analyzed by using the analyzer of the invention shown in FIG. 3. The appearance of the analyzer is shown by the photograph for the apparatus in FIG. 10.

EXAMPLE

The present invention is to be described more specifically by way of examples but the invention is not restricted to the examples.

Example 1

Analysis for Interaction Between a Glycan and a Lectin Utilizing a Lectin Array (1) Preparation of Fluorescence-Labeled Glycan Protein Probe (Cy3-ASF)

A fluorescence-labeled glycoside protein probe was prepared by fluorescence-labeling Asialo-Fetuin (manufactured by SIGMA Co. hereinafter referred to as ASF) using Cy3 Mono-reactive Dye (manufactured by Amersham Pharmacia Biotech Co. hereinafter referred to as Cy3) as a fluorescent dye having an absorption maximum wavelength near 550 nm. It is known that ASF has a glycan structure having an N-binding type glycan and an O-binding type glycan each by the number of 3 in the molecular and in which sialic acid cap at the non-reducing terminal in the glycan is partially detached. After preparing ASF to a final concentration of 1 mg/mL in a 0.1 M carbonate buffer (pH 9.3), it was mixed with 1.0 mg of a Cy3 powder per 1 mL, which was reacted in a dark place for 1 hour under optional stirring.

Then, free Cy3 and Cy3-ASF were recovered by separation by a gel filtration chromatography using Sephadex G-25 as a carrier and the concentration and the fluorescence labeling efficiency were measured for the purified Cy3-ASF by using an absorption photometer. The yield on the protein base was 35 to 40%, and the fluorescence labeling efficiency (number of fluorescent dye per one protein molecule) was about 3.0.

(2) GTMS Coating to Slide Glass

Using a slide glass coated with 3-glysidoxypropyl trimethoxysilane having epoxy groups as an active group (manufactured by Shin-etsu Silicone Co. hereinafter referred to as GTMS) (FIG. 1), lectins were immobilized to the surface the glass. The GTMS coating was conducted by the following procedures using a slide glass manufactured by Matsunami Glass Industry Co., the slide glass was dipped into a 10% KOH/MeOH solution and left for 1 hour in a state being shaken together with a container to treat the glass surface. After washing the same with a sufficient amount of pure water (milli Q water), it was dried in an oven at 60° C., then, the slide glass was dipped in a 2% GTMS acetone solution and reacted for 1 hour while being shaken together with the container or vessel under a light shielding. After the reaction and after drying in an oven at 110° C. for 8 hours, it was washed with sufficient amount of pure water and then dried.

(3) Immobilization of Lectins to Slide Glass (2) Lectins were spotted to the slide glass applied with the GTMS coating (2). STAMPMAN manufactured by Nippon Laser & Electronics Lab Co., Ltd. was used as a microarray spotter and spotting was conducted by using a stamp pin with a diameter at the top end of 0.40 mm to arrange spots of about 0.6 to 0.7 mm in diameter on the slide. Each of the lectins to be spotted was dissolved in a phosphate buffer physiological saline at pH 7.4 (hereinafter referred to as PBS) to a concentration of 1 mg/mL (0.25 mg/mL for some spots depending on the lectin). This was dispensed each by 10 µL to each of the reaction vessels of a 96 hole PCT micro titer plate (Corning Co.), which was set to the micro array spotter.

Upon procedure of immobilizing lectins to the slide glass, the following conditions were stored in a computer appended to the microarray spotter and a stamp pin operation program was executed. At first, after dipping the stamp pin into an immobilizing specimen solution in the 96-hole PCT micro titer plate for 1 sec and then it was pulled up and brought into contact with a predetermined position on the surface of the slide glass for 1 sec. While repeating the operation on every spot, after spotting for 4 points in one lateral row from an identical specimen solution, a cleaning step was applied to the stamp pin. In the cleaning step, the needle tip of the stamp pin was dipped in a 0.05% SDS solution for 2 sec, the stamp pin was dried in a vacuum device for 15 sec, further, dipped in pure water for 2 sec, then dried in a vacuum device for 15 sec and, finally, dipped into ethanol for 2 sec and, then applied with a drying operation in the vacuum device for 15 sec.

In this example, five types of proteins in total, that is, four types of lectins having various glycan glycoside-binding specificities (RCA 120, SSA, xylane binding domain of xylanase derived from recombinant actinomycetes (hereinafter referred to as XBD) and C terminal end side domain derived from recombinant earth worm 29 kDa lectin (hereinafter referred to as EW 29 (Ch)) and one type of negative control (hereinafter referred to as BSA) were spotted. RCA 120 and BSA purchased from SIGMA Co., SSA purchased from Biochemical Industry Co. and XBD, EW 29 (Ch) expressed and purified from Bacterium coli in the research laboratory of the present inventors were used.

(4) Blocking for Non-Spotted Surface

After reacting the lectin solution for 1 hr after the spotting treatment and immobilizing the same on a glass surface, unbonded lectins were cleaned. In the cleaning, a PBS solution (PBST) containing 0.1% Tween 20 was applied by spraying to the slide glass for several times by a pipette for cleaning, and it was further cleaned sufficiently by using PBS.

Figure 11:
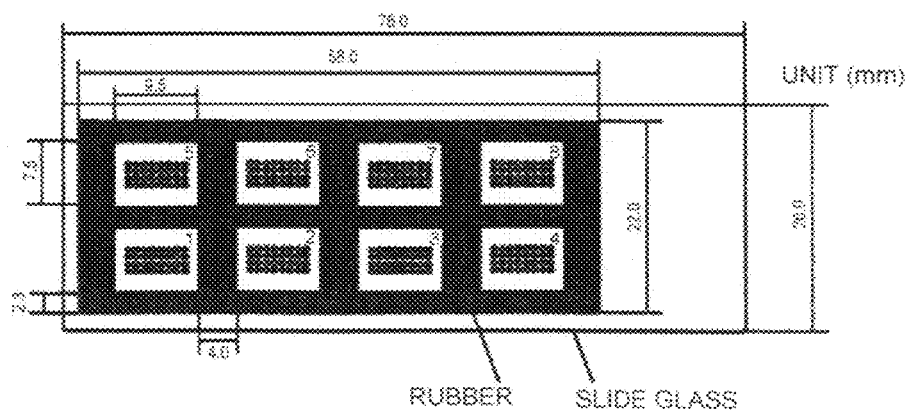
FIG. 11 is a view showing a substrate formed with eight reaction vessels used in this example.

For the slide glass after immobilization of the lectins, a 8-hole rubber designed and developed by the inventors is bonded at a predetermined position to manufacture an eight reaction vessels (FIG. 11). The 8-hole rubber is made of black silicone rubber of 1 mm thickness in which eight rectangular holes each of 9.5×7.5 mm in length and width are opened regularly and 8 reaction vessels can be formed when bonded to the slide glass. When a specimen of about 50 µL is applied to the reaction vessel, the inside can be filled with a sufficient amount of the specimen solution.

Since the epoxy groups as the active groups were remained on the glass surface other than the regions spotted with the lectins, blocking operation was applied to the non-spotted surface. For a blocking agent, highly pure BSA (SIGMA) was used. A PBS solution containing 1% BSA was filled each by 50 µL to the inside of eight reaction vessels, left at 4° C. for 1 hour in a preservation vessel kept at a humidity of 90% or higher to conduct blocking to the non-spotted surface on the slide glass. During reaction, care was taken so as to prevent drying on the glass surface.

Then, the blocking solution on the slide glass was removed and, after sufficiently cleaning by using PBS, water content was removed. In order to prevent denaturation of the protein due to drying at the glass surface or increase of the background along with drying, it was forwarded to the next operation as soon as possible after immobilization of the protein.

(5) Addition of Probe Solution and Scanning

A probe solution of a fluorescence-labeled glycoside protein intended to be analyzed for the interaction was added to the reaction vessel on the lectin immobilizing slide glass prepared in (4). The probe for the fluorescence labeled glycoside protein was prepared by dissolving in PBS so as to be at a final concentration of 10 µg/mL and dropped by 50 µL to each of the reaction vessels.

After standing still, till the reaction between lectin and glycan reached equilibrium, an excitation light was entered from the end face of the slide glass by using GTMAS Scan III as an evanescent excitation type microarray scanner (manufactured by Nippon Laser & Electronics Lab Co., Ltd) and the fluorescence emission generated by excitation was detected by an ICCD camera disposed to the lower surface of the slide glass. After scanning fluorescent images substantially for the entire surface of the slide glass obtained images were stored by a TIFF file form (about 100 MB per one sheet). The parameter during scanning was made uniform to "5000 times" of Gain, "four times" of accumulation cycles, and "33 msec" of exposure time.

(6) Digitalization of Scanning Images

For the digitalization of scanning images, Array-Pro Analyzer as a commercial microarray analyzer software (version 4.0 for Windows (registered trade mark), manufactured by Media Cybernetics Co.) was used. The luminance for each spot was calculated by using the analyzer software described above, and the luminance at the non-spotted region was defined as a background value. The luminance for each of the spots subtracted with the background value was defined as a net luminance value and an average value and a standard deviation were calculated on every spot derived from identical specimen for 4 points arranged in a lateral row.

For the binding of the probe to each of the lectin specimens, evaluation was conducted hereinafter by using the average luminance value for 4 spots derived from the identical specimen. The performance evaluation for each of the lectin arrays shown below was conducted after by way of a series of steps of the procedures (2) to (6).

(7) Performance Evaluation for GTMS Coated Slide Glass

The performance of the GTMS coated slide glass manufactured as described above was evaluated in comparison with existent slide glass (6 types). That is, previously Cy3-labeled lectin (100 µm/mL) was immobilized in an array to each slide glass applied with a surface coating and after by way of the steps (3) to (6), the S/N ratio was calculated based on the luminance value (S) for the spotting region and the luminance value (N) for the non-spotting surface. As a result, as shown in Table 1 while the luminance value for the GTMS coated slide glass manufactured by the step (2) remained at about ½ of the slide glass A showing the highest value, since the background was extremely low, the S/N was 16.1 showing the best value among the slide glass evaluated in this time.

TABLE 1

Performance evaluation for each slide glass
100 µg/ml Cy3 RCA-120 in 30% glycerol/PBS

|  | Average value for 4 spots points (Gain × 1000)$^{NOTE}$ | Average value for 4 blanks (Gain × 1000)' | S/N ratio |
|---|---|---|---|
| Commercial slide glass A | 60617 | 5971 | 10.2 |
| Commercial slide glass B | 52059 | 4013 | 13.0 |
| Commercial slide glass C | 36452 | 2856 | 12.7 |
| GTMS slide glass | 28220 | 1753 | 16.1 |
| Commercial slide glass D | 13138 | 4520 | 3.1 |
| Commercial slide glass E | 12802 | 3105 | 4.1 |
| Commercial slide glass F | 5902 | 1621 | 3.6 |

$^{NOTE}$Average luminance value for identical Cy3-labeled lectin spots was compared.

Figure 12:
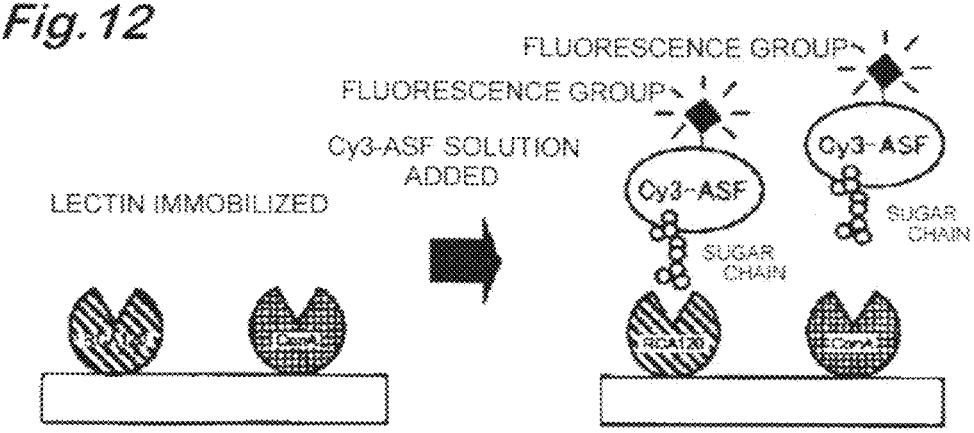
FIG. 12 is a conceptional view of a performance experiment for a lectin array in which a Cy3-AFS solution is added on an array where two types of lectins are immobilized.
Figure 13:
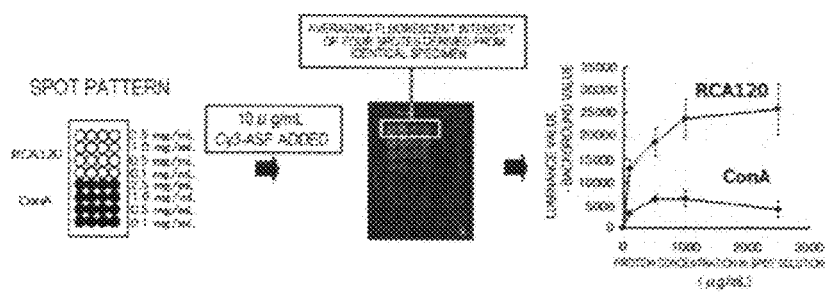
FIG. 13 is a view and a photograph showing a relation between a concentration of a lectin solution and a florescent intensity of spots upon immobilization.

(8) Investigation on Immobilized Lectin Concentration on Array (FIGS. 12 and 13)

RCA 120 and ConA are typical lectins known to have high affinity to complex glycans and high mannose type glycans, respectively. The lectins were prepared in various concentrations, and spotted in an array each being arranged at four points laterally for an identical specimen. After applying 10 µg/mL of Cy3-ASF each by 50 µL to each of the reaction vessels in the array and causing binding reaction, fluorescence was observed by a scanner.

As described above, it has been known that ASF has a glycan structure having N-binding type glycans and O-binding type glycan each by three in the molecule and in which sialic acid at the non-reducing terminal in the glycan is decapped to protrude the lactosamine structure. Accordingly, in an experimental system of adding Cy3-ASF to the lectin array formed by immobilizing RCA 120 and ConA, it was expected that RCA 120 shows an extremely strong affinity, while ConA shows a weak affinity.

As a result of the experiment, while the spot of RCA 120 emitted a strong fluorescence, the ConA spot showed only about ⅓ of the fluorescent intensity compared with the spot of RCA 120 under the identical condition. It was considered that ConA was bonded though weak to ASF having the complex type glycan because it could not be bonded to the three chain type glycan mainly present IN ASF among the N-binding type glycan but it could be bonded to the 2-chain type glycan which was considered to be present in a small amount. Further, it has been found from the data that the standard deviation (SD) for four points derived from the identical specimen was about ±20% (FIG. 13).

Then when the relation between the lectin concentration and the fluorescent intensity upon spotting was expressed as a graph, it was found that a positive correlation existed between the lectin concentration upon spotting and the fluorescent intensity and the signal intensity could be improved efficiently by increasing the concentration of the lectin specimen to be spotted to 1 mg/mL or higher. That is, it was found that the interaction between the lectin and the glycan of small affinity constant (weak binding) could be detected by increasing the concentration of the immobilized lectin (FIG. 13).

(9) Performance Evaluation for Lectin Array 5 types of proteins in total, that is, four types of lectins (RCA 120, SSA, XBD, EW 28 (Ch)) having various glycoside specificities and one type of negative control (BSA) were arranged at four spots laterally for one identical specimen and spotted in an array. Cy3-ASF of 10 µg/mL was dropped to the array each by 50 µL and the fluorescence was observed by a scanner.

Figure 14:
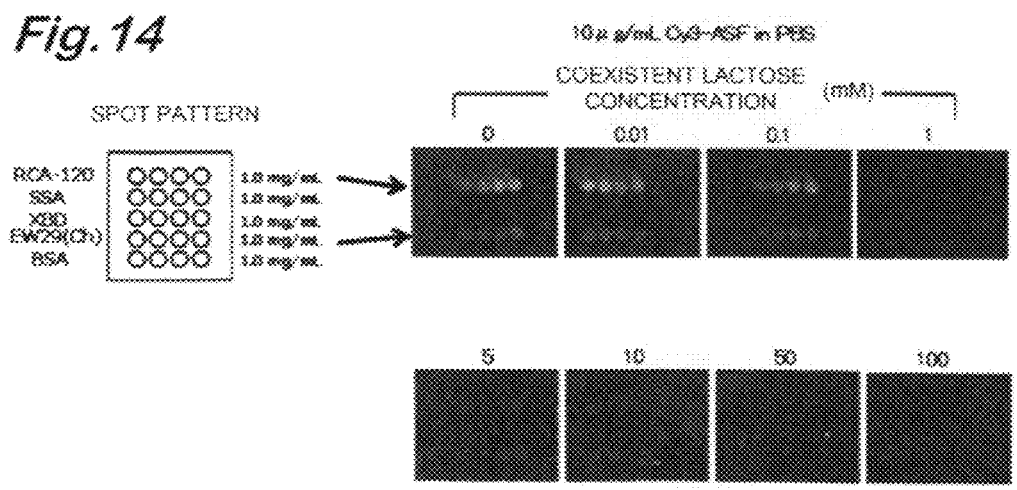
FIG. 14 is a view and a photograph showing detection of interaction between a lectin and a glycan and the effect on the interaction by an inhibitory glycan.

As a result of the experiment, fluorescence signals were observed in the spots of two types of lectins of RCA120 and EW 29 (Ch) for which affinity to the lactosamine structure could be confirmed by a frontal affinity chromatography (FAC) (FIG. 14). Further, when the fluorescent intensity was compared for each of them, an intense fluorescence was observed for the spots of RCA 120, while a medium fluorescence was observed for the spots of EW 29 (Ch), and this agreed with the FAC analysis data.

Figure 15:
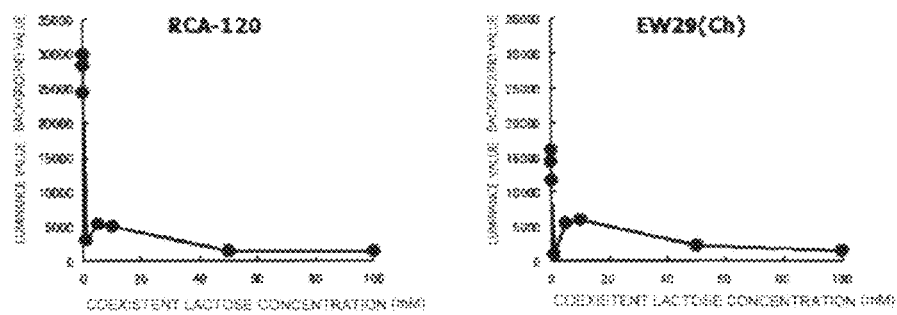
FIG. 15 is a view showing the effect of the inhibitory glycan on the lectin-glycan interaction as a graph.

Further, when an identical experiment was conducted for the array under the identical conditions in the co-existence of lactose (competition inhibitory glycan), degrease of the fluorescent intensity for the spots was observed along with increase in the concentration of the inhibitory glycan (FIG. 15). It could be confirmed from this that binding with the fluorescent glycoside protein probe is due to the glycan specific binding reaction between lectin and the glycan.

Example 2

Figure 16:
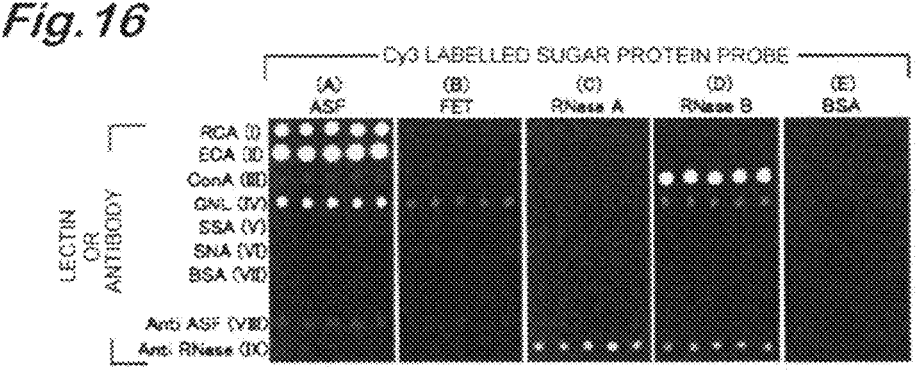
FIG. 16 is a photograph showing an example of a lectin-antibody hybrid array.

Analysis by Hybrid Array Spotting Lectin-Antibody in One Identical Compartment (FIG. 16)

1. Material and Method
(1) Preparation of Fluorescence Labeled Probe of Model Glycoside Protein In this experimental example, as lectins to be immobilized on a lectin array, 6 types (RCA120, ECA, ConA, GNA, SSA, SNA) were selected as lectins having various glycan binding specificity. Further, BSA as a protein not binding with the glycan was selected as a negative control. Further, in this experiment, two types of anti-fetuin antibody and anti-RNase antibody recognizing the core protein portion of the probe were spotted in a compartment identical with that of the lectin. GNA and SNA purchased from VECTOR Co., BSA purchased from SIGMA Co., and RCA120, ECA, ConA, SSA purchased from Biochemical Industry were used.

A model fluorescence-labeled glycoside protein probe was prepared by fluorescence-labeling ASF, FET, ribonuclease B (RNase B) derived from bovine pancreas, and ribonuclease A (RNase A) derived from bovine pancreas, and protein such as BSA as negative control (all purchased from SIGMA Co.) by using Cy3 Mono-reactive Dye as a fluorescence dye having an absorption maximum wavelength near 550 nm (manufactured by Amersham Pharmacia Biotech hereinafter referred to as Cy3). Upon preparing the probe, after preparing the protein described above to a final concentration of 1.0 mg/mL in a 0.1 M carbonate buffer (pH 9.3), it was mixed with 1.0 mg of Cy3 powder, reacted for 1 hour in a dark place under optional stirring, and Cy3-labeled protein was purified by gel filtration chromatography using Sephadex G-25 as a carrier.

(2) GTMS Coating on Slide Glass

Lectins were immobilized on the glass surface by using a slide glass coated with 3-glycidoxy propyl trimethoxysilane having epoxy groups as active groups (manufactured by Shin-etsu Silicone Co., hereinafter referred to as GTMS) (FIG. 1). GTMS coating was applied by the following procedures using a slide glass manufactured by Matsunami Glass Industry Co. The slide glass was dipped in a 10% KOH/MeOH solution and left for one hour in a state being shaken together with the vessel to treat the glass surface. After washing the same with a sufficient amount of pure water (milli Q water), it was dried in an oven at 60° C. Then, the slide glass was dipped into a 2% GTMS acetone solution and reacted for 1 hour under shielding of light while being shaken together with the vessel. After the reaction and after drying in an oven at 110° C. for 8 hours, it was washed with a sufficient amount of pure water and dried.

(3) Manufacture of Lectin Array

Lectins were spotted to the GTMS coated slide glass manufactured in (2) to manufacture a lectin array. As a microarray spotter, STAMPMAN manufactured by Nippon Laser & Electronics Lab Co., Ltd. was used and spots of about 0.5 mm diameter were arranged on the slide glass by using a stamp pin with a top end diameter of 0.40 mm.

Upon procedure of immobilizing lectins to the slide glass, the following conditions were stored in a computer appended to the microarray spotter and a stamp pin operation program was executed. At first, after dipping the stamp pin into an immobilizing specimen solution in the 96-hole PCR micro titer plate for 1 sec and then it was pulled up and brought into contact with a predetermined position on the surface of the slide glass for 1 sec. While repeating the operation on every spot, after spotting for 6 points in one lateral row from an identical specimen solution, a cleaning step was applied to the stamp pin. In the cleaning step, the needle tip of the stamp pin was dipped in a 0.05% SDS solution for 2 sec, the stamp pin was dried in a vacuum device for 15 sec, further, dipped in pure water for 2 sec, then dried in a vacuum device for 15 sec and, finally, dipped into ethanol for 2 sec and, then applied with a drying operation in the vacuum device for 15 sec.

(4) Blocking of the Non-Spotted Surface

A 8-hole rubber made of silicone rubber was adhered on the slide glass spotted with lectins by the procedures described above to manufacture eight reaction vessels. By filling the reaction vessels with a PBS solution containing 0.1% Tween 20 (PBST), excess lectins not bonded to the slide solid layer were cleaned and removed. Then, after filling a PBS solution dissolving 1% BSA therein each by 200 µL to each of the reaction vessels, they were left for 1 hour in a preserving vessel kept at a humidity of 90% or higher at 4° C. to conduct blocking procedure for the non-lectin spotted region.

(5) Addition of Probe Solution and Scanning

Each of the fluorescence-labeled glycoside protein probe solution adjusted to about 100 mg/mL was added each by 50 µL to each of the reaction vessels to the slide after completing the blocking, thereby contacting the probe solution on the array.

After standing still, till the reaction between lectin and glycan reached equilibrium, an excitation light was entered from the end face of the slide glass by using GTMAS Scan III as a evanescent excitation type microarray scanner (manufactured by Nippon Laser & Electronics Lab Co., Ltd) and the fluorescence emission generated by excitation was detected by an ICCD (charge coupled device with image intensifier) camera disposed to the lower surface of the slide glass. After scanning fluorescent images substantially for the entire surface of the slide glass obtained images were stored by a TIFF file form. The parameter during scanning was made uniform to "4000 times" of Gain, "8 times" of accumulation cycles, and "110 msec" of exposure time.

(6) Digitalization of Scanning Images

For the digitalization of scanning images, Array-Pro Analyzer as a commercial microarray analyzer software ver. 4.5 (manufactured by Media Cybernetics Co.) was used. The luminance for each spot was calculated by using the analyzer software described above, and the luminance at the non-spotted region was defined as a background value. The luminance for each of the spots subtracted with the background value was defined as a net luminance value and an average value and a standard deviation were calculated on every spot derived from identical specimen for 5 points arranged in a lateral row.

Subsequently, for the binding of the probe to each of the lectin specimens, evaluation was conducted by using the average luminance value for five spots derived from the identical specimen.

2. Result and Consideration

In the experiment described above, arrays in which lectins having various specificity were manufactured and the performance as the lectin array was evaluated based on the fluorescence pattern for each of the lectin spots upon applying the glycoside protein probe having known glycan structure. In this experiment, with an aim of acquiring also the information for the core protein portion of the probe simultaneously, a hybrid array in which antibodies recognizing the core protein portion of the glycoside protein probe were also spotted along with lectins. As model glycoside proteins, a combination of ASF and FET and a combination of RNase A and RNase B were selected as proteins having identical structure for the core protein portion but different in the structure for the modified glycan portion.

In experiments (A), (B), glycan profiles of ASF and FET used as the probes were compared (FIGS. 16A and B). It has been known that FET has N-binding type glycans and O-binding glycans each by the number of 3 in the molecule, and the non-reducing terminal for each of the glycan structures is highly modified with sialic acid. On the other hand, ASF is a protein which the terminal end sialic acid in the FET glycan is removed by enzymatic or acid treatment to expose a lactosamine structure.

Accordingly, it was expected that in a case of using the ASF probe, spots for RCA 120 and ECA recognizing the lactosamine were observed and spots for SSA and SNA recognizing the sialic acid were observed in a case of using the FET probe. Further, since the core protein portion is identical to the antibody spot both for FET and ASF, it was expected that binding was observed for both the probes. As a result of the experiment, while extremely bright spots of RCA 120 and ECA were detected for the ASF probe having the terminal lactosamine structure (FIG. 16A), the spots for RCA 120 and ECA were extremely dark in the FET probe capped with sialic acid for the lactosamine structure (FIG. 16B). The result agreed with the existent knowledge that RCA 120 and ECA strongly recognized the lactosamine structure and the affinity was lowered greatly when the terminal of the lactosamine structure was capped with the sialic acid. Further, in the experiment (B), spots for SSA and SNA as the sialic acid recognition lectin were observed corresponding to the presence of sialic acid characteristic to the FET probe (FIG. 16B). In the spots for ConA, weak fluorescence was observed both in the experiments (A) and (B) (FIGS. 16A and B). It is considered that although they could not be bonded to the 3-chain type glycan mainly present in the N-binding type glycan, they could be bonded to the 2-chain type glycan considered to be present in a small amount. In the spots for the FET antibody recognizing the common core protein portion, fluorescence was observed in the experiments (A) and (B) (FIGS. 16A and B).

In the experiments (C) and (D), difference of the glycan profiles was compared between the RNase A and RNase B (FIGS. 16C and D). It has been known that RNase B has one high mannose type N-binding type glycan in the molecule, while RNase A has an identical structure with RNase B for the core protein portion, but has no glycan at all. It was expected that in a case of contacting the probe with the lectin array, both the probes showed affinity to the anti RNase antibody spot but resulted in difference in the reactivity to the lectin spot (while RNase B probe shows affinity with mannose recognition lectin ConA but RNase A has no such affinity). As a result of the experiment, for the reactivity to the antibody, binding with the RNase antibody recognizing the common core protein portion was observed in both of the probes. On the other hand, for the reactivity to the lectin, while binding was observed in the ConA spot for the RNase B having the high mannose structure, fluorescence due to binding was not observed in the lectin spot for the RNase A not having the glycan. In the experiment (E), BSA as the protein not having the glycan was used as a negative control. For the BSA probe, binding was not observed both for the antibody and lectin spot as expected (FIG. 16E).

Through the experiments (A) to (E), profiles reflecting the glycan binding specificity of lectin could be obtained rapidly from a microamount of glycan protein specimen (FIGS. 16A to E). Further, in this experiment, by spotting the lectin and the antibody on one identical array, information on the core protein portion and the modified glycan portion of the glycoside protein could be acquired simultaneously in parallel on one sheet of slide. Further, by conducting analysis simultaneously in parallel on one slide, it resulted in an advantage that observation was possible in the state of making the experimental conditions (temperature, reaction time, etc.) uniform between each of the reaction vessels.

Example 3

Figure 17:
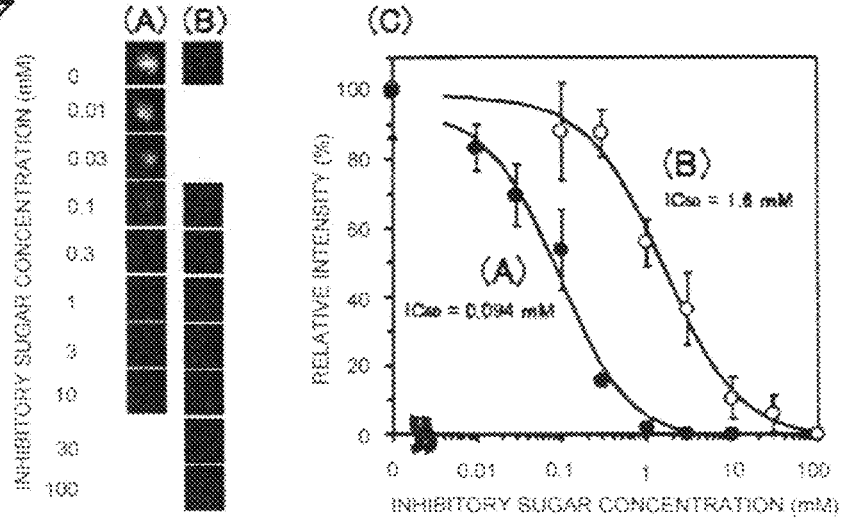
FIG. 17 is a photograph and a view showing a result of observation for the inhibition on the interaction by using eight reaction vessels with coexistence of inhibitory glycan at different concentrations on one identical slide. (A) is a case of adding lactose to the binding of RCA 120 and ASF binding, (B) is a case of adding mannose to the binding of ConA and RNaseB.

Inhibitory Concentration Analysis Using Lectin Array (FIG. 17)

1. Material and Method

For confirming that the binding between lectin and probe molecules observed in the experiment was specific binding by way of the glycan, an inhibitive experiment using a competitive inhibitory glycan was conducted. In the experiment (A), RCA 120 was spotted in eight reaction vessels on a slide glass to constitute an array, then 8 types of ASF probe solutions with the concentration of a competitive inhibitory glycan (lactose) being changed were contacted simultaneously to observe the inhibition for the binding reaction (FIG. 17A). In the experiment (B), using ConA as the immobilizing lectin, using RNase B as the probe, and using mannose as the competitive inhibitory glycan, inhibition for the binding was observed by the same procedures (FIG. 17B). Since the materials and the procedures required for manufacturing the array were identical with those in the Example 2, descriptions therefor are to be omitted.

2. Result and Consideration

As a result of the experiment, decrease in the fluorescent intensity of the spots was observed along with increase in the concentration of the competitive inhibitory glycan (FIG. 17), and one-half inhibitory concentration inherent to the inhibitory substance could be calculated by curve-fitting an inhibition curve. From the result, it could be confirmed that binding with the fluorescent glycoside protein probe is due to the specific binding reaction between the lectin and the glycan. Further, it was shown that evaluation for the intensity of the binder by the calculation of the one-half inhibitory concentration or search for mating binding molecules were possible by using such inhibitory experiment.

Example 4

Figure 18:
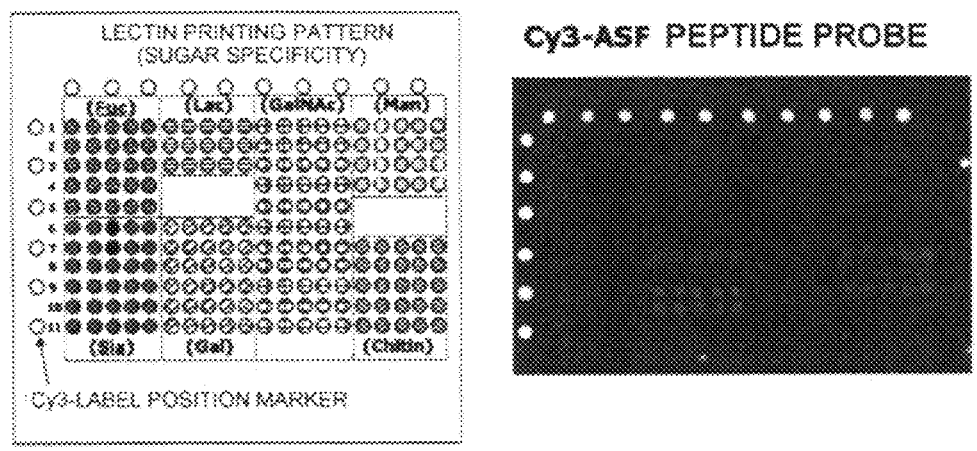
FIG. 18 is a view and a photograph showing the result of an experiment using a glycoside peptide probe for the detection of a lectin array.

Detection of Lectin Array Glycan Peptide Probe (FIG. 18)

1. Material and Method
(1) Preparation of Glycoside Peptide Probe

After preparing Cy3-ASF by the method described in Example 2(1), Cy3-ASF was fractioned by a trypsin treatment to prepare Cy3-ASF peptide.
(2) GTMS Coating to Slide Glass It was conducted by the method described in Example 2(2).
(3) Manufacture of Lectin Array For lectins to be immobilized, after grouping them on every main glycan recognizing ability for each of the lectins, 40 types of lectins in total were selected, that is, 5 types of fucose recognition lectin, 6 types of sialic acid recognition lectin, 3 types of lactosamine structure recognition lectin, 6 types of glactose recognition lectin, 11 types of a galactosamine recognition lectin, 4 type of mannose recognition lectin, and 5 types of chitin structure recognition lectin, and they were immobilized on a slide glass to manufacture arrays. The experimental procedures were conducted by the method described in Example 2(3).
(4) Blocking of Non-Spotted Surface
(5) Addition of Probe Solution and Scanning
(6) Digitalization of Scanning Images For the procedures (4) to (6), the Cy3-ASF peptide probe was used and experiment was conducted by the same procedures as the method described in Example 2(4) to (6).
2. Result and Consideration As a result of the experiment, by serving the glycoside peptide probe to the lectin array, glycan profiles reflecting the glycan structures could be obtained. The obtained glycan profile was identical with ASF before enzymatic digestion showing that not only the glycoside protein but also peptide digestion products of the glycoside protein can be utilized for the lectin array. By utilizing the technique of fractionating the glycoside peptide by HPLC or the like and then using them as a probe for the lectin array, the glycan profile for each of the ingredients of the glycoside peptide can be observed and this is useful.

Example 5

Figure 19:
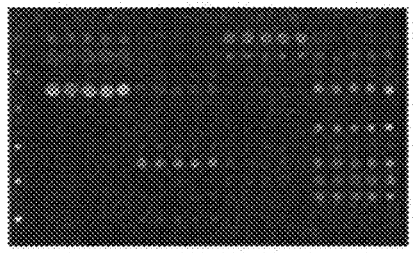
FIG. 19 is a photograph showing the result of analysis by a lectin array upon forming crude specimens derived from living bodies into probes.
Figure 19:
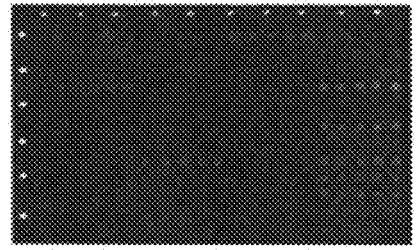
Figure 19:
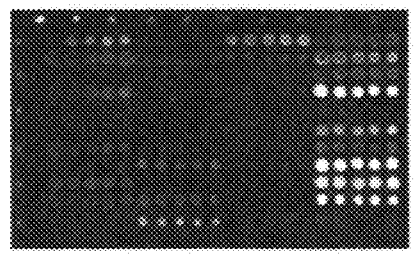

Experiment Using Crude Biospecimen as a Probe to Lectin Array (FIG. 19)

1. Material and Method

The glycan addition state of the invivo glycoside protein is analyzed by conducting glycan profile for a glycoside protein mixture, particularly, biobody-derived mixture specimen by using the lectin array.

After Cy3 labeling a glycoside protein sample extracted and purified from mouse liver and a glycoside protein sample extracted and purified from mouse brain into probes, they were brought into contact with lectin arrays in which 40 types of lectins were immobilized to observe the glycan profiles for the entire mouse extracted glycoside protein mixture.

Since the materials and the procedures required for manufacturing the array were identical with those in Example 2, descriptions thereof are to be omitted.
2. Result and Consideration In the mouse brain-derived glycoside protein probe (FIG. 19A) and liver-derived glycoside protein probe (FIG. 19B), apparently different glycan profiles were observed. Particularly, in the sialic acid recognition lectin groups, a distinct difference was observed between both of the probes. It has been known that sialic acid is less added to the glycoside protein in the brain and the fact agreed with the trend of the result of the experiment. Since the glycan addition information for the entire specimen can be obtained rapidly and simply also in the experiment using the crude specimen as described above, this is suitable to the use with an aim of comparatively analyzing the difference of the glycan structures between individuals or between pathologic conditions of blood ingredients or organs all at once, also in the experiment using such crude specimens.

10 mM of lactose was added as a competitive inhibitory glycan to the brain-derived glycoside protein probe used in the previous experiment and the glycan profile was observed (FIG. 19C). As a result, change was observed in the pattern of the fluorescence signals by competitive inhibition and decay of signals of lactosamine recognition lectin was mainly observed. As shown by the experiment, also in the glycan profiling by lectin array to more crude specimens, comparative analysis can be conducted between individuals more simply and rapidly by conducting comparative analysis in combination with an addition experiment of various inhibitory glycans and restriction of the acquired information.

Example 6

Figure 20:
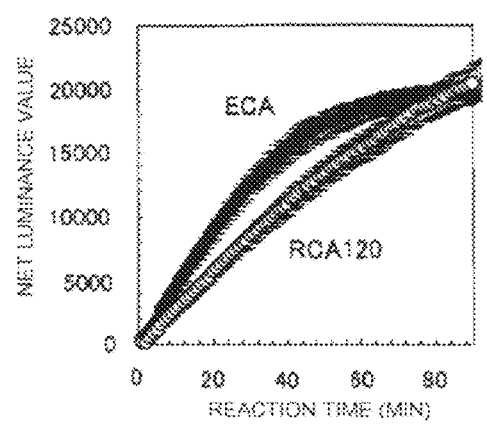
FIG. 20 is a view observing the change with time of a net signal intensity upon reacting 100 ng/mL of Cy3-ASF probe to two types of lectin (RCA 120, ECA), by using a real time scanning function.

Observation with Time for Interaction Between Lectin and Glycoside Protein (FIG. 20)

Since interaction in the liquid layer can be observed in an equilibrium state as it is with no requirement for cleaning step upon scanning according to this apparatus, observation with time (real time scanning) for binding and dissociation reaction of interaction is possible by observing the change of the signal intensity with time from the start of the reaction.

100 ng/mL of Cy3-ASF was added as a fluorescence glycoside protein probe in a reaction vessel to a substrate where various types of lectins of different specificity were immobilized, and the change with time of the signal intensity just after the start of the binding reaction was observed. Since other experimental conditions overlap with those in Example 1, they are not described. In this experiment, scanning was conducted at a scanning interval of 60 sec. As a result, difference in the binding reaction rate due to the difference in the reaction rate was observed (FIG. 20). Such reaction time scanning is useful not only for enabling the observation for the reaction rate but also for finding a final end point of the equilibrium reaction under the measuring conditions.

Example 7

Figure 21:
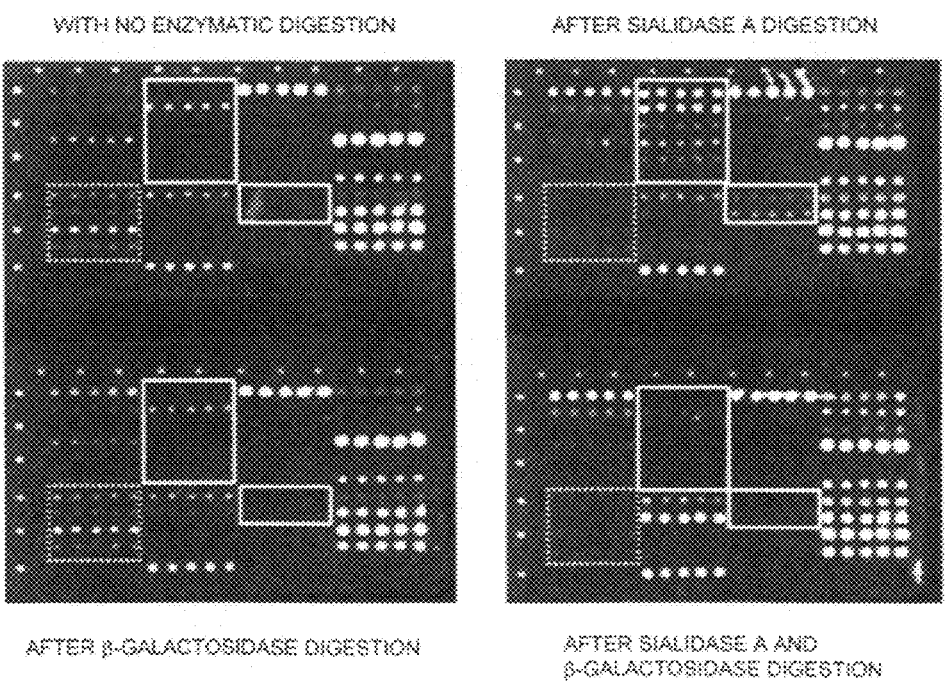
FIG. 21 is a view showing the change of a glycan profile of bovine transferin by glycoside hydrolase digestion. Solid line: lectin observed for signal increase by enzymatic digestion. Dotted line: lectin observed for signal lowering by enzymatic digestion.

Estimation Method for the Glycan Structure of Glycoside Protein Using Enzymatic Digestion (FIG. 21)

1. Material and Method
(1) Preparation and Enzymatic Digestion of Glycoside Protein Probe After preparing Cy3 labeled bovine transferrin (Cy3-bTf) by the method described in Example 2 (1), Cy3-bTf was digested with glycoside hydrolase (sialidase A or β galactosidase).

(2) GTMS Coating on Slide Glass

It was conducted by the method described in Example 2 (2).

(3) Manufacture of Lectin Array

For lectins to be immobilized, after grouping them on every main glycan recognizing ability for each of the lectins, 40 types of lectins in total were selected, that is, 5 types of fucose recognition lectin, 6 types of sialic acid recognition lectin, 3 types of lactosamine structure recognition lectin, 6 types of glactose recognition lectin, 11 types of a galactosamine recognition lection, 4 type of mannose recognition lectin, and 5 types of chitin structure recognition lectin, and they were immobilized on a slide glass to manufacture arrays. The experimental procedures were conducted by the method described in Example 2 (3).

(4) Blocking of Non-Spotted Surface
(5) Addition of Probe Solution and Scanning
(6) Digitalization of Scanning Images For the procedures (4) to (6), Cy3-bT enzyme digestion product probe was used and experiment was conducted by the same procedures as the method described in Example 2(4) to (6).

2. Result and Consideration

As a result of the experiment, by serving the glycoside protein probe subjected to each of glycoside hydrolyzing enzymatic treatment to the lectin array, glycan profile reflecting the glycan structure of the reaction products could be obtained (FIG. 21). In a case of sialidase A digestion, a significant fluctuation of the profile was shown before and after the reaction but the reaction products of β galactosidase showed substantially identical profile with the not reacted glycoside protein (FIG. 21). This shows that almost non-reducing terminals of the N-binding type glycan of bTf undergoes sialic acid modification. By comparing the glycan profiles before and after the enzymatic reaction based on the substrate specificity of each of the glycoside hydrolase as described above, the glycan structure of the target glycoside protein could be estimated more exactly.

Reference Example 1

Figure 22:
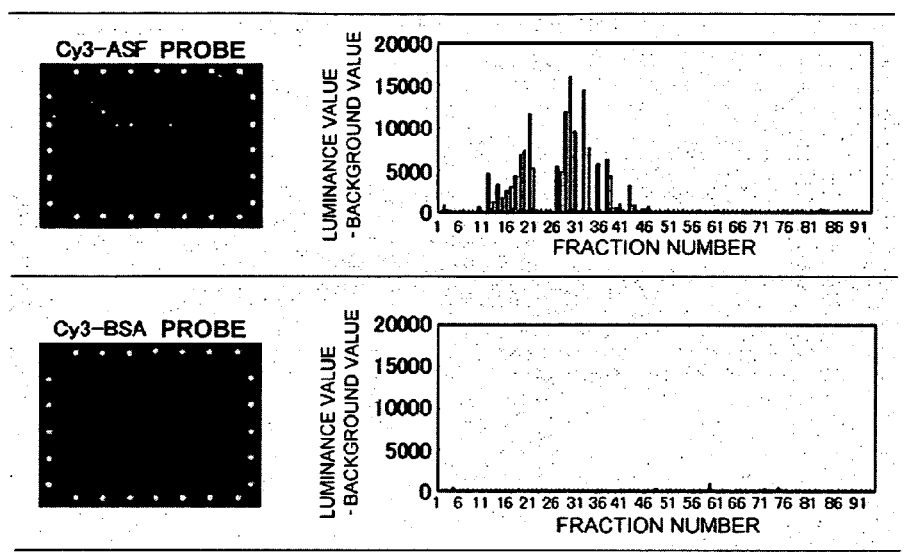
FIG. 22 is a view and a photograph showing the result of an experiment for detecting glycoside peptide array formed by immobilizing HPLC fraction of a mouse liver-derived glycoside peptide sample. In the figure, Fuc for fucose recognition lectin group, Sia for sialic acid recognition lectin group, Lac for lactose recognition lectin group, Gal for galactose recognition lectin group, GalNAc for N-acetyl galactosamine recognition lectin group, Man for mannose recognition lectin group, and Chitin for chitin recognition lectin group.

Glycan Profiling of Glycoside Peptide by Glycoside Peptide Array (FIG. 22)

1. Material and Method
(1) Preparation of Lectin Probe

In this example, RCA 120 intensely recognizing the lactosamine structure was used as a lectin probe and BSA not having the glycan binding ability was used as the negative control. The fluorescence-labeled lectin probe was prepared by fluorescence-labeling using Cy3 as a fluorescence dye. After dissolving the lectin to a final concentration of 10 mg in a 0.1 M carbonate buffer (pH 9.3), it was mixed with 1.0 mg of a Cy3 powder per 1 mL and reacted for 1 hour in a dark place under optional stirring. After the reaction, unreacted Cy3 dye was removed by using an ultrafiltration filter kit.

(2) GTMS Coating on Slide Glass

GTMS coated slide was conducted by the method described 1(2).

(3) Manufacture of Glycoside Peptide Array

A glycoside peptide array was manufactured by spotting a glycoside peptide to the GTMS coated slide glass manufactured in (2) (FIG. 1). Spots of about 0.5 mm diameter were arranged on a slide glass by spotting using STAMPMAN manufactured by Nippon Laser & Electronics Lab Co., Ltd as a microarray spotter using a stamp pin with a top end diameter of 0.40 mm.

In this experiment, as an immobilized glycoside peptide sample, a glycoside peptide formed by segmenting a glycoside protein fraction purified from a soluble fraction of mouse liver by using a lectin column into peptide fragments and then fractionation and isolation them by HPLC was used. Upon immobilizing operation of the glycan peptide on the slide glass, the following conditions were stored in a computer appended to a microarray spotter and a stamp pin operation program was executed. At first, after dipping a stamp pin into an immobilized specimen solution in a 96-hole PCT micro titer plate, it was pulled up and brought into contact at a predetermined position on the surface of the slide glass for 1 sec. While repeating the operation on every one spot, after spotting at 6 points in one lateral row from one identical specimen solution, stamp pin was cleaned. In the cleaning step, the needle tip of the stamp pin was immersed in a 0.05% SDS solution for 2 sec, the stamp pin was dried in a vacuum device for 15 sec, then further dipped in pure water for 2 sec, dried in the vacuum device for 15 sec and, finally, dipped in ethanol for 2 sec and then applied with a drying procedure in the vacuum device for 15 sec.

(4) Blocking of Non-Spotted Surface
(5) Addition of Probe Solution and Scanning
(6) Digitalization of Scanning Images For the procedures (4) to (6), Cy3-RCA 120 probe and Cy3-BSA probe was used and experimental procedure was conducted in accordance with the method described in Example 2(4) to (6).

2. Result and Consideration

The result of the experiment showed that the structural information of the glycan added to the glycoside peptide could be obtained at a high throughput and easily by arranging the glycoside peptide into an array. As a method of manufacturing the glycoside peptide array, it may be considered, for example, (1) immobilization of purified glycoside peptide, (2) immobilization of crude glycoside peptide, or (3) immobilization of a glycoside peptide fraction separated by HPLC. In this experiment, respective fractions separated by HPLC formed into an array could be manufactured and their usefulness could be shown.

Heretofore, it was not easy to obtain an information as to where the glycoside peptide was contained in the fractions fractionated by HPLC since this could not be monitored, for example, by UV absorption or fluorescence. The result of this experiment revealed that it could easily be recognized that which fractions comprise glycan peptides having what kind of glycan by using the array in which each of the glycoside peptide fractions is immobilized.

Since it is possible to rapidly obtain information as to which fraction contains a glycoside peptide having a glycan as a target of analysis by utilizing this method, it is possible to select only the fractions containing the glycans efficiently from a number of fractions and serve them to another analysis such as mass analysis. Further, in a case where there is no information on the glycan structure of a glycoside peptide as a target of analysis or there is no information on what type of lectin is bonded, lectins binding to the glycoside proteins could be refined from several tens types of lectins by conducting the analysis using the lectin array in a state of the glycoside protein before trypsin digestion and conducting glycan profiling. By obtaining such information, procedures such as lectin plotting which were conducted in a round-robin manner so far by using a plurality of lectins can be simplified to provide a merit capable of greatly saving time and labors.

Reference Example 2

Application to Other Glycan Concerned Arrays

Figure 23:
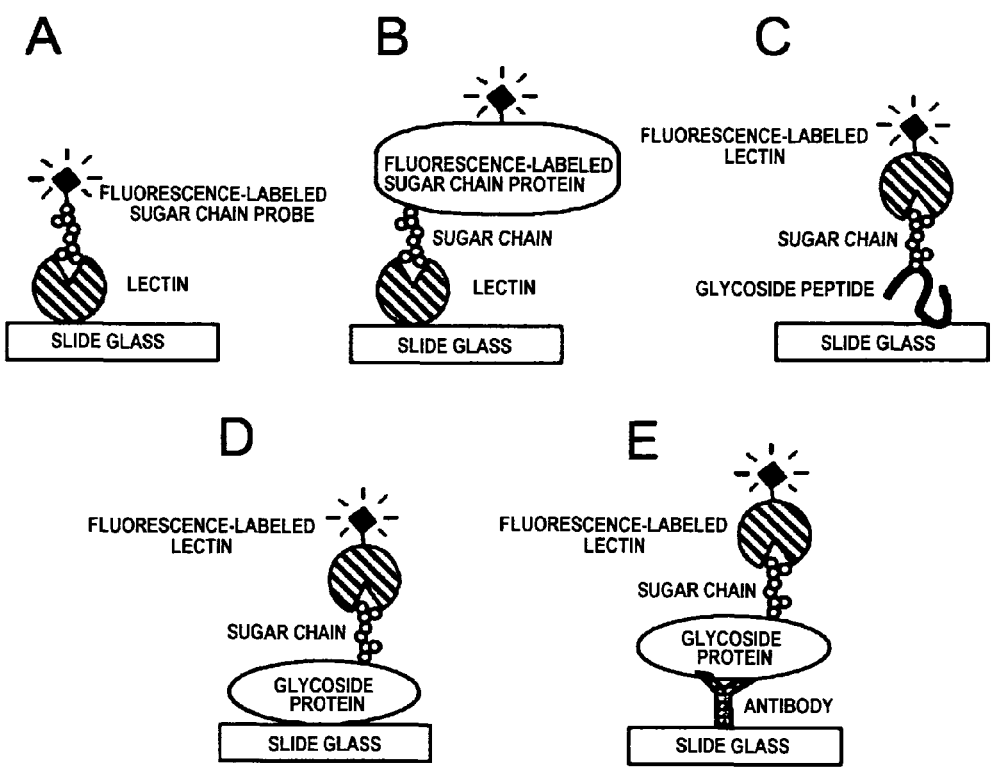
FIG. 23 is a schematic view showing the binding state of each of glycan concerned arrays and glycans. A: a schematic view showing the binding state of a probe to the array in a case of using a lectin array and a glycans as the probe. B: a schematic view showing the binding state of a probe to the array in a case of using a lectin array and a glycoside protein as a probe. C: a schematic view showing the binding state of a probe to the array in a case of using a glycoside peptide array and lectin as a probe. This can be used for reducing the glycan structure in the fractioned peptide. D: a schematic view showing the binding state of a probe to the array in a case of using a glycoside protein array and lectin as a probe. E: is a schematic view showing the binding state of the probe to the array in a case of using an antibody array and lectin as the probe.

Glycan concerned arrays include a lectin array using the glycan for the probe, as well as a lectin array using glycoside protein for a probe, a glycoside peptide array using lectin for a probe, a glycoside protein array using lectin for a probe and an antibody array using lectin as a probe. FIG. 23 shows a schematic view for the interaction between various glycan concerned arrays and glycans.

The invention claimed is:

1. An analyzer for fluorescence-labeling a glycan to be detected or a complex carbohydrate to be detected with or without purification, for measuring the binding state of the glycan or the complex carbohydrate and a protein thereby, and for analyzing the glycan to be detected or the complex carbohydrate to be detected, or a specimen containing the same, the analyzer including,
   a substrate comprising:
      a rectangle photoconductive base plate coated by a compound containing an active group to fix protein by an amino group thereof,
      plural open-topped reaction vessels arranged in a matrix with plural columns in a direction along a short side of the base plate and formed on a surface of the base plate, and
      plural spots of glycan binding proteins arranged in a matrix and immobilized on the surface of the base plate in the reaction vessel;
   a fluorescent labeling exciter, which excites fluorescent label by generating evanescent-waves on the surface of the substrate, comprising a pair of optical fibers arranged toward both right and left side end faces as long sides of the substrate to introduce a light symmetrically in a direction along the short side thereinto; and
   a fluorescent intensity measurer for measuring the intensity of fluorescence generated by the fluorescent labeling exciter on each of the spots of the glycan binding protein.

2. The analyzer according to claim 1, wherein the surface of the photoconductive base plate is covered by a light blocking rubber opening holes at the positions corresponding to areas of the reaction vessels so that the reaction vessels are formed in areas of the holes.

3. The analyzer according to claim 1, wherein the surface of the photoconductive base plate is coated by a water-repellent material except for the areas corresponding to the reaction vessels so that the reaction vessels are formed in areas surrounded by the water-repellent material.

4. The analyzer according to claim 1, wherein the glycan binding protein is a lectin or a glycan recognition antibody belonging to an IgM class.

5. The analyzer according to claim 1, wherein the substrate is one in which the glycan binding proteins are arranged and immobilized in a predetermined pattern in accordance with the type thereof.

6. The analyzer according to claim 1, wherein an antibody to a portion other than the glycan of the complex carbohydrate are arranged and immobilized together with the glycan binding protein on the substrate.

7. The analyzer according to claim 1, having a memory for storing the fluorescent intensity measured by the fluorescent intensity measurer on every position of arranging the glycan binding proteins corresponding to the glycan to be detected or the complex carbohydrate to be detected that are used.

8. The analyzer according to claim 1, having a memory for storing the measured fluorescent intensity divided by steps on every position of arranging the glycan binding protein.

9. The analyzer according to claim 8, having an indicator for indicating the fluorescent intensity divided stepwise on every type of each of the glycan binding proteins.

10. The analyzer according to claim 1, wherein the substrate is one in which multiple types of identical glycan binding proteins are arranged and immobilized on every type thereof.

11. The analyzer according to claim 10, having a calculator and memory for calculating and storing an average value of the fluorescent intensity measured for identical glycan binding proteins.

12. The analyzer according to claim 11, having a memory for storing stepwise average values of fluorescent intensities measured for identical glycan binding proteins.

13. The analyzer according to claim 12, having an indicator for indicating stepwise the fluorescent intensities being divided on every type of the glycan binding proteins.

14. The analyzer according to claim 7, wherein the fluorescent intensity information for known glycans or complex carbohydrates are stored in the memory.

15. The analyzer according to claim 8 wherein the fluorescent intensity information for known glycans or complex carbohydrates are stored in the memory.

16. The analyzer according to claim 11, wherein the fluorescent intensity information for known glycans or complex carbohydrates are stored in the memory.

17. The analyzer according to claim 12, wherein the fluorescent intensity information for known glycans or complex carbohydrates are stored in the memory.

18. The analyzer according to claim 14, having a selector for matching the fluorescent intensity information for a glycan or a glycoside protein as a target of analysis to the fluorescent intensity information for known glycans or complex carbohydrates, and selecting an identical or approximate glycan or complex carbohydrate.

19. The analyzer according to claim 15, having a selector for matching the fluorescent intensity information for a glycan or a glycoside protein as a target of analysis to the fluorescent intensity information for known glycans or complex carbohydrates, and selecting an identical or approximate glycan or complex carbohydrate.

20. The analyzer according to claim 16, having a selector for matching the fluorescent intensity information for a glycan or a glycoside protein as a target of analysis to the fluorescent intensity information for known glycans or complex carbohydrates, and selecting an identical or approximate glycan or complex carbohydrate.

21. The analyzer according to claim 17, having a selector for matching the fluorescent intensity information for a glycan or a glycoside protein as a target of analysis to the fluorescent intensity information for known glycans or complex carbohydrates, and selecting an identical or approximate glycan or complex carbohydrate.

\* \* \* \* \*